United States Patent
Petitpierre et al.

(10) Patent No.: US 12,114,917 B2
(45) Date of Patent: Oct. 15, 2024

(54) ENDOLUMINAL NERVE MODULATION DEVICE AND METHODS FOR USING THEREOF

(71) Applicant: ECOLE POLYTECHNIQUE FEDERALE DE LAUSANNE (EPFL), Lausanne (CH)

(72) Inventors: Guillaume Petitpierre, Veyrier (CH); Philippe Renaud, Préverenges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 363 days.

(21) Appl. No.: 16/303,795

(22) PCT Filed: May 10, 2017

(86) PCT No.: PCT/IB2017/052731
§ 371 (c)(1),
(2) Date: Nov. 21, 2018

(87) PCT Pub. No.: WO2017/203380
PCT Pub. Date: Nov. 30, 2017

(65) Prior Publication Data
US 2020/0315700 A1 Oct. 8, 2020

(30) Foreign Application Priority Data
May 24, 2016 (WO) .................. PCT/IB2016/053030

(51) Int. Cl.
*A61B 18/14* (2006.01)
*A61B 18/00* (2006.01)
*A61B 18/12* (2006.01)

(52) U.S. Cl.
CPC ...... *A61B 18/1492* (2013.01); *A61B 18/1206* (2013.01); *A61B 2018/00136* (2013.01);
(Continued)

(58) Field of Classification Search
CPC .. A61B 2018/00404; A61B 2018/0041; A61B 2018/00416; A61B 2018/00422;
(Continued)

(56) References Cited

U.S. PATENT DOCUMENTS

| 3,547,103 A | 12/1970 | Cook |
| 4,757,827 A | 7/1988 | Buchbinder et al. |

(Continued)

FOREIGN PATENT DOCUMENTS

| AU | 2010208618 B2 | 8/2010 |
| WO | 2015/164912 A1 | 11/2015 |

OTHER PUBLICATIONS

Yuba Raj Limbu et al., Assessment of carotid artery dimensions by ultrasound in non-smoker healthy adults of both sexes, Sep. 8, 2006. (Year: 2006).*

(Continued)

*Primary Examiner* — Linda C Dvorak
*Assistant Examiner* — Nicholas S Borsch
(74) *Attorney, Agent, or Firm* — Nixon & Vanderhye P.C.

(57) ABSTRACT

The invention provides for a device (100) for use in electrical nerve modulation in a subject, characterized in that it comprises a rotational and linear actuator (110); a tubular element (101) having a proximal end connected to the actuator (110) and a distal end; a flexible shaft (102) coaxially disposed within the tubular element (101), comprising a proximal end operably connected to the actuator (110) and a distal end, and adapted to be slid along the tubular element (101); a conformable support (103) comprising a proximal end operably connected to the tubular element's (101) distal end, and a distal end operably connected to the flexible shaft's (102) distal end, having a portion of its length helically wrapped about a distal portion of the flexible shaft (102) so to define a pitch (500) and a (Continued)

radius (400); and a plurality of electrodes (104) operably disposed along the helically configured portion of the conformable support (103), and electrically connectable to a generator (200), adapted to contact the endoluminal surface of a blood vessel of the subject and deliver electrical energy; wherein the pitch (500), radius (400) or both of the helically configured portion of the conformable support (103) can be modified via actuator's (110) driven extension, retraction and/or rotation of the flexible shaft (102).

16 Claims, 19 Drawing Sheets

(52) U.S. Cl.
CPC ............ *A61B 2018/00404* (2013.01); *A61B 2018/00434* (2013.01); *A61B 2018/00511* (2013.01); *A61B 2018/1253* (2013.01); *A61B 2018/126* (2013.01); *A61B 2018/1435* (2013.01); *A61B 2018/1495* (2013.01)

(58) Field of Classification Search
CPC .......... A61B 2018/00428; A61B 2018/00434; A61B 2018/0044; A61B 2018/00446; A61B 2018/1405; A61B 2018/1435; A61B 2018/144; A61B 2018/1407; A61B 2018/141; A61B 17/221; A61B 17/32056; A61B 2017/00212; A61B 2017/12054; A61B 2017/12059; A61B 2017/12063; A61B 2017/12068; A61B 2017/12072; A61B 2017/12077; A61B 2017/12081; A61B 2017/12086; A61B 2017/1209; A61B 2017/12095; A61B 2018/1495; A61B 18/1492; A61B 18/1206; A61B 2018/00136; A61B 2018/00511; A61B 2018/1253; A61B 2018/126; A61B 2018/00214; A61B 2018/00345; A61B 2018/00654; A61B 2018/00696; A61B 2018/00702; A61B 2018/00708; A61B 2018/00714; A61B 2018/0072; A61B 2018/00726; A61B 2018/00732; A61B 2018/00738; A61B 2018/00744; A61B 2018/0075; A61B 2018/00755; A61B 2018/00761; A61B 2018/00767; A61B 2018/00773; A61B 2018/00779; A61B 2018/00785; A61B 2018/00791; A61B 2018/00797; A61B 2018/00803; A61B 2018/00809; A61B 2018/00815; A61B 2018/00821; A61B 2018/00827; A61B 2018/00833; A61B 2018/00839; A61B 2018/00845; A61B 2018/00851; A61B 2018/00857; A61B 2018/00863; A61B 2018/00869; A61B 2018/00875; A61B 2018/0088; A61B 2018/00886; A61B 2018/00892; A61B 2018/00642; A61B 2018/00648; A61N 1/36185; A61N 1/36117; A61N 1/36017; A61N 1/0558; A61N 1/0551
See application file for complete search history.

(56) References Cited

U.S. PATENT DOCUMENTS

| | | | |
|---|---|---|---|
| 5,203,772 | A | 4/1993 | Hammerslag et al. |
| 5,228,442 | A * | 7/1993 | Imran ................ A61N 1/056 600/374 |
| 6,322,559 | B1 * | 11/2001 | Daulton ............ A61B 18/1492 606/41 |
| 2001/0037084 | A1 | 11/2001 | Nardeo |
| 2005/0119614 | A1 | 6/2005 | Melsky |
| 2006/0135961 | A1 | 6/2006 | Rosenman et al. |
| 2006/0241519 | A1 | 10/2006 | Hojeibane et al. |
| 2008/0027285 | A1 | 1/2008 | Yasunaga |
| 2011/0224769 | A1 * | 9/2011 | Spenser ................ A61M 25/04 607/149 |
| 2012/0071870 | A1 * | 3/2012 | Salahieh ............ A61B 1/00181 606/33 |
| 2012/0245577 | A1 * | 9/2012 | Mihalik ............ A61B 18/1492 606/33 |
| 2012/0271140 | A1 * | 10/2012 | Kordis ................ A61B 5/283 600/375 |
| 2014/0005706 | A1 * | 1/2014 | Gelfand ................ A61N 7/022 606/169 |
| 2014/0052109 | A1 | 2/2014 | Organ et al. |
| 2014/0180307 | A1 | 6/2014 | Shalev et al. |
| 2014/0276747 | A1 * | 9/2014 | Abunassar ......... A61B 18/1492 607/101 |
| 2014/0277310 | A1 * | 9/2014 | Beetel .................. A61N 1/0551 607/116 |
| 2014/0343538 | A1 | 11/2014 | Lenker et al. |
| 2015/0065945 | A1 * | 3/2015 | Zarins ................ A61B 18/04 514/183 |
| 2015/0126992 | A1 | 5/2015 | Mogul |
| 2015/0230859 | A1 * | 8/2015 | Mauch ............... A61B 18/1492 606/41 |
| 2015/0289770 | A1 * | 10/2015 | Wang ................ A61B 5/0036 606/41 |
| 2016/0206853 | A1 | 7/2016 | Bolduc et al. |
| 2016/0250449 | A1 | 9/2016 | Hansen |
| 2017/0252103 | A1 * | 9/2017 | Greifeneder ....... A61B 18/1492 |
| 2017/0296798 | A1 * | 10/2017 | Kume ................ A61M 39/24 |

OTHER PUBLICATIONS

Aleksander Prejbisz et al., Smaller caliber renal arteries are a novel feature of uromodulin-associated kidney disease, Feb. 15, 2015 (Year: 2015).*
Annotated Fig 5A (Year: 2023).*
Jaroslaw Krejza, MD, PhD et al, Carotid Artery Diameter in Men and Women and the Relation to Body and Neck Size, 2006 (Year: 2006).*
Kapil, Vikas, et al., "Renal Sympathetic Denervation—A Review of Applications in Current Practice," Resistant Hypertension, Interventional Cardiology Review, 2014, pp. 54-61.
Sathananthan, Janarthanan, et al., "Renal sympathetic denervation: indications, contemporary devices and future directions," Review, Interv. Cardiol., vol. 6, No. 1, 2014, pp. 57-69.
International Search Report for PCT/IB2017/052731 dated Aug. 24, 2017, 7 pages.
Written Opinion of the ISA for PCT/IB2017/052731 dated Aug. 24, 2017, 7 pages.
Communication pursuant to Article 94(3) EPC dated Feb. 15, 2021, issued in European Application No. 17808142.8, 8 pages.

* cited by examiner

Possible configurations after release:

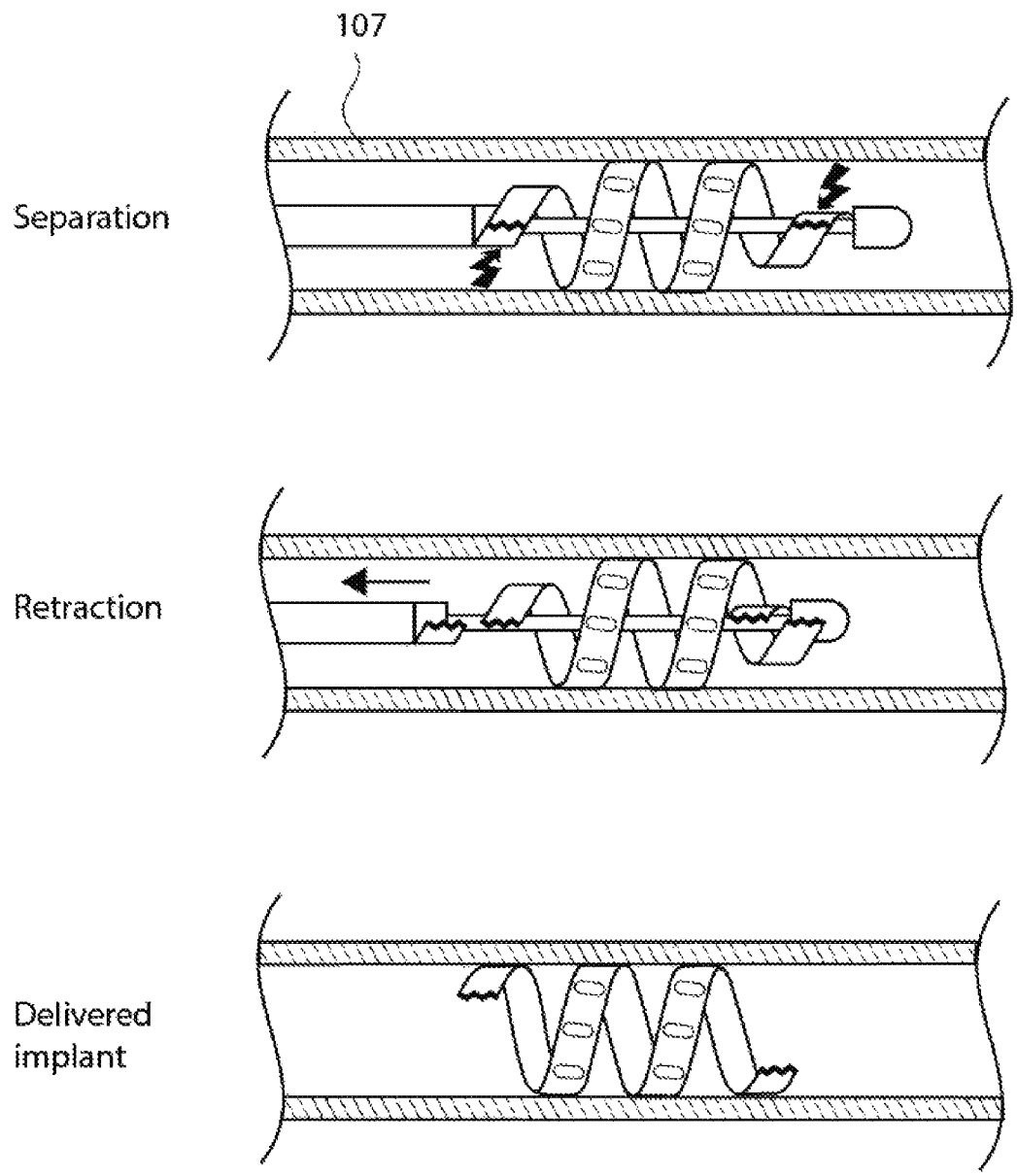

ENDOLUMINAL NERVE MODULATION DEVICE AND METHODS FOR USING THEREOF

This application is the U.S. national phase of International Application No. PCT/IB2017/052731 filed May 10, 2017 which designated the U.S. and claims priority to International Application No. PCT/IB2016/053030 filed May 24, 2016, the entire contents of each of which are hereby incorporated by reference.

TECHNICAL FIELD

The present invention relates to nerve electrical modulation, and particularly to devices and methods for treating pathological conditions in which such a modulation could be beneficial.

BACKGROUND ART

A common, relatively recent approach for the treatment of pathological conditions in which the sympathetic nervous system plays a key role is the so called nerve ablation or denervation. The autonomic nervous system, a division of the peripheral nervous system, is a network of nerves that influences and controls the functions of internal organs. For instance, it is responsible for regulating body functions such as the control of the respiration, cardiac regulation, vasomotor activity and certain reflex actions. The system is mainly composed of two branches, the sympathetic and parasympathetic nerves. In the kidney sympathetic innervation, the efferent sympathetic nerve originate from the spinal cord, cross the sympathetic chain, and reach the celiac ganglia. From this ganglia, the postganglionic efferent fibres project along the renal artery (at the periphery) to finally innervate the kidney Within the renal nerves are included the post-ganglionic efferent sympathetic nerves and the afferent nerves from the kidney. These latter travel within the dorsal root (if they are pain fibers) and into the anterior root (if they are sensory fibers), then into the spinal cord and ultimately to specialized regions of the brain. The afferent nerves, relaying the signals of the baroreceptors and chemoreceptors, deliver information from the kidneys back to the sympathetic nervous system center in the brain; their ablation, partial disruption or inhibition is at least partially responsible for the improvement seen in blood pressure after renal nerve ablation. It has also been suggested and partially proven experimentally that the baroreceptor response at the level of the carotid sinus is mediated by the renal artery afferent nerves such that a loss of the renal artery afferent nerve response blunts the response of the carotid baroreceptors to changes in arterial blood pressure (DiBona et al., American J. Physiology and Renal Physiology 279:F491-F501, 2000).

Renal denervation is a minimally invasive, endovascular catheter based procedure using radio-frequency (RF) ablation or ultrasound ablation aimed at treating refractory hypertension (high blood pressure not controlled by medication). Nerves of the sympathetic nervous system adjacent to the renal artery in the wall of this latter are ablated by applying radio-frequency electrical energy or ultrasound energy to the renal arteries, causing local tissue heating. This is a relatively new procedure, which has been found to be clinically effective in treating hypertension, but that is also associated with a significant amount of pain. Existing treatments can be both relatively difficult for the physician to be accurately perform and quite time-consuming.

Many medical devices have been brought to the market for the treatment of refractory hypertension through renal denervation. For instance, The Symplicity™ renal denervation system consists of a generator and a flexible catheter. During a minimally invasive procedure, the physician uses the catheter that emits RF energy across multiple electrodes. The RF energy is delivered to a renal artery via standard femoral artery access. A series of 1-minute ablations are delivered along each renal artery to disrupt the nerves, with typically 4 to 6 ablations performed serially, in a distal to proximal fashion in a helical pattern. During energy delivery, the tip of the catheter induces heating between 70° C. to 90° C. in the subjacent tissue.

The EnligHTN™ System is a multi-electrode catheter-based device delivering RF energy with an ablation pattern. An RF ablation generator simultaneously activates four evenly spaced electrodes, activated in monopolar mode, disposed on a basket which allegedly allow consistent placement of ablation electrode sets so to enable repeatable results when the device is displaced along the renal artery for several RF pulses applications.

The Boston Scientific's Vessix V2™ Renal Denervation System comprises a low-pressure (3 atm) non-compliant balloon catheter with radio-frequency gold bipolar electrodes and thermistors mounted on the external surface.

The Covidien's OneShot™ System features an irrigated balloon-based platform with a helical electrode on its surface to deliver a single radio-frequency treatment per artery. Other systems are known in the art such as the Recor's Paradise™ System, the Terumo's Iberis™ System and the Cordis Corporation's RENLANE™ Renal Denervation System.

All the above described systems for treating hypertension through a renal denervation approach have been specifically developed bearing in mind the specific pathology and the peculiar anatomy of the body portions to be treated. However, all these systems have several structural and functional limitations in terms of efficacy and "universality". For example, even if theoretically usable in bi-multipolar mode, the electrodes are used only in a monopolar modality (excepted for the Boston Scientific V2™). This is mainly linked to the aim of the therapy, the environment where the electrodes work and the arrangement thereof in/on the device. As will be evident to a skilled in the art, since RF energy shall be directed towards the walls of the vessel in order to ablate the nerves wrapped therealong, single electrodes disposed along a basket, an elongated or a solenoid-like structure, and inserted endovascularily, cannot be practically used in bi-multipolar mode in order to avoid dissipation of RF energy towards the lumen of the vessel, and possible formation of blood clots due to overheating of the blood itself. A balloon-like architecture, even if possibly eliminating this issue, blocks the lumen of the blood vessel, thus impairing the blood flow. Therefore, once the electrodes are activated, specific-patterned, single energy spots are delivered towards the internal vessel wall, which are not supposed to guarantee the ablation of the nerves due to the unpredictable path thereof along the vessels. Moreover, all the above-described systems lack of universality, due to rigid or semi-rigid scaffolds supporting the electrodes, which impose limitations in terms of size of the vascular area to be treated and are therefore only suitable for renal denervation of adult patients.

A device for use in nerve ablation by applying RF energy to the endoluminal surfaces of a patient's arteries, having a more universal design, is described in US 2015/0126992. The document discloses a catheter apparatus carrying RF ablation electrodes on a helically configured portion of a flexible tube that can be inserted into the femoral artery of a patient, advanced into a renal artery, and then manipulated to properly position the electrodes carried by the helical tube to contact the endoluminal surface of an artery, particularly the renal artery. A low level of RF energy can be applied to selected sites on the endoluminal surface of the artery in order to ablate the renal sympathetic nerves without affecting the abdominal, pelvic, or lower-extremity nerves. The catheter comprises a flexible, soft, multi-lumened distal shaft tube carrying RF-ablation electrodes, temperature sensors and associated connecting wires on/in a helically-coiled portion (including an imbedded a pre-fanned mechanical wire) of the length thereof, a less soft, flexible single or multi-lumened proximal shaft tube, a flexible sliding tube or rod (a so-called "slider"), and a handle with an actuating mechanism and cable assembly/connector.

In use, with the distal end of the catheter inserted into position within an artery to be treated, the operating technician or physician will move the slider rightwardly to withdraw the rod, thereby pulling the distal end of the catheter toward the handle, collapsing the helix and thereby reducing the pitch and increasing the radius of the coiled tube, and thus changing the longitudinal and radial loci of the several electrodes. This device is adaptable in theory to several different artery calibres due to the possibility to regulate the deployment of the active electrical elements therein, that facilitate the fitting to various vessels' geometries. However, even in this case several structural constraints limit the optimal use in a denervation approach, namely the impossibility to practically use the electrodes in bi-multipolar mode and to modify at the physician's discretion the pitch between the electrodes. Moreover, the device is clearly not suitable when the internal geometry of the vessel is not constant all along its length, such as in case of stenosis of a portion of the vessel.

Intracranial aneurysm is a condition in which an external cavity, bubble-like, occurs on a cerebral artery wall which is filled with blood. If the cavity increases in size, there is a strong risk of rupture. In case of rupture, blood leaks in the cerebral tissues and has devastating consequences. This bleeding is called Subarachnoid Haemorrhage (SAH). This is a severe condition which affects 660'000 persons annually, worldwide (de Rooij et al., J Neurol Neurosurg Psychiatry; 78:1365-1372, 2007)

The most dangerous complication after SAH is the cerebral vasospasm (CVS). It affects 64% of the patients after SAH (angiographically confirmed) representing 420'000 cases per year (Hofmann et al., ISRN Vascular Medicine, Volume 2011, Article ID 782568). CVS is characterized by an abnormal spasmodic constriction of the cerebral arteries (punctual or diffused) which leads to a lack of oxygen and the death of cerebral tissues. CVS generally occurs 5 to 10 days after SAH, but the risk remains high during 21 days. CVS is highly dangerous, difficult to detect and to treat. It is responsible for 23% of mortality or severe morbidity after SAH (Keyrouz and Diringer, Crit Care; 11(4):220, 2007). The current therapies are ineffective, risky and restricted to specific brain areas. A better way to treat CVS is a strong unmet medical need.

The physiopathological mechanism leading to CVS is complex. Blood exposition in the subarachnoid space leads to a cascade of effects based on enzymatic activation triggering the release of spasmodic agents (vehiculated via OxyHb, for instance). However, many studies also demonstrates that the sympathetic system plays a major role in the development of CVS (Goellner and Slavin, Med. Hypotheses, vol. 73, no 3, 410-413, 2009; Karadağ et al., Acta Neurochir (Wien), 147: 79-84, 2005; Treggiari et al., Stroke; 34:961-967, 2003). From this perspective, it is clear that SAH leads to the sympathetic system imbalance and tissue inflammation which result in the development of cerebral vasospasm.

Posterior grey matter of the hypothalamus is the nuclei of the sympathetic system. Preganglionic neurons project from this nuclei, through the spinal cord, to the superior cervical ganglion (SCG). It is a major element of the sympathetic system chain which further projects postganglionic neurons to the internal carotid arteries. It there forms a plexus of nerves which follow the internal carotid artery and direct to different elements such as the pterygopalatine ganglion, the ciliary ganglion and, ultimately, reach the cerebral arteries, as represented in FIG. 7. Sympathetic nervous system stimulation causes vasoconstriction of most blood vessels, including in the brain. This occurs as a result of activation of alpha-1 adrenergic receptors, present in the vascular wall of blood vessels, by norepinephrine released by post-ganglionic sympathetic neurons. The vasomotor action which consists in vasoconstriction or vasodilation of the blood vessels is mainly controlled by the perivascular sympathetic fibers travelling around veins and arteries. These nerves act on smooth muscle cells from the tunica media, the middle layer of the vessels walls, provoking contraction or dilation of the wall.

A strong involvement of sympathetic system in animal models of vasospasm was demonstrated (de Souza Faleiros et al., Arq. Neuropsiquiatr., vol. 64, no 3A, 572-574 2006; Kezdi P., Circ. Res., vol. 2, no 4, 367-371, 1954). Accordingly, electrical stimulation of the spinal cord at the location where the efferent fibers leave to later converge into the SCG was also demonstrated to increase the cerebral blood flow in case of vasospasm (Goellner and Slavin, Med. Hypotheses, vol. 73, no 3, 410-413, 2009; Takanashi and Shinonaga, Neurol. Med. Chir. (Tokyo), vol. 40, no 7, 352-357, 2000). Several studies also showed the involvement of the cerebrovascular innervation in the development of cerebral vasospasm (Edvinsson et al., J. Cereb. Blood Flow Metab., vol. 10, no 5, 602-607, 1990; Shiokawa and Svendgaard, J. Auton. Nerv. Syst., vol. 49, Supplement, 167-170, 1994). In the 1970's, it was suggested that medical procedures consisting in the ablation of carotid plexus nerves could be beneficial to stop CVS progression in patient affected by SAH.

Without being bounded to this theory, it is thought that after a traumatic event such as SAH the sympathetic system is over-activated, resulting in the development of cerebral vasospasm. Modulating or otherwise inhibiting this abnormal sympathetic activity through electrical modulation or nerve ablation during or preferably before the development of CVS could allow to prevent its apparition. This would lead to a novel therapy for the treatment of vasospasm.

SUMMARY OF INVENTION

In order to address and overcome the several drawbacks of the prior art solutions in the field of nerve modulation/ablation, the inventors conceived and created a novel device for use in an endovascular setting having a universal design for what concern the structural elements in direct contact with the internal wall of a blood vessel. Thanks to a rotational and linear actuation of a flexible shaft included in a catheter-like element, a conformable support adapted to contact the internal wall of a blood vessel can be suitably put in contact with the bodily structures of a subject so to deliver a nerve modulation input therein, particularly with a plurality of electrodes patterned on the support. This latter has a helical configuration, wherein the pitches of the helix structure can be reconfigured according to the compelling needs, thanks to extension, retraction and/or rotation of the flexible shaft triggered by the actuator. Particularly, a key feature of the device of the invention resides in its possibility to modify independently or at the same time, if needed, both the pitch and the radius of the helical support, so to specifically tailor the position and/or the distribution of the electrodes in contact with the blood vessel and therefore the electrical nerve modulation, while adapting the design of the support to any size or internal geometry of the target vessel. Therefore, the pitch can be adjusted for any given radius, thus further avoiding any mechanical stress exerted on the vessel wall.

Accordingly, it is an aim of the present invention to provide for a device for use in electrical nerve modulation in a subject, characterized in that it comprises:
  a) a rotational and linear actuator;
  b) a tubular element having a proximal end connected to the actuator and a distal end;
  c) a flexible shaft coaxially disposed within the tubular element, comprising a proximal end operably connected to the actuator and a distal end, and adapted to be slid along the tubular element;
  d) a conformable support comprising a proximal end operably connected to the tubular element's distal end, and a distal end operably connected to the flexible shaft's distal end, having a portion of its length helically wrapped about a distal portion of the flexible shaft defining a pitch and a radius; and
  e) a plurality of electrodes operably disposed along the helically configured portion of the conformable support, and electrically connectable to a generator, adapted to contact the endoluminal surface of a blood vessel of the subject and deliver electrical energy
  wherein the pitch, radius or both of the helically configured portion of the conformable support can be modified via actuator's driven extension, retraction and/or rotation of the flexible shaft.

In one embodiment, the device is characterized in that the conformable support is substantially made of one or more soft polymeric materials.

In one embodiment, the device is characterized in that the electrodes are compliant.

In one embodiment, the device is characterized in that the plurality of electrodes are bundled in groups of electrodes.

In one embodiment, the device is characterized in that the electrodes are activated in a mono-, bi- or multipolar fashion.

In one embodiment, the device is characterized in that the actuator is operated through manual means, hydraulic means, pneumatic means, electromechanical means, computer-aided means or combinations thereof.

In one embodiment, the device is characterized in that it further comprises a generator operably connected to the plurality of the electrodes.

In one embodiment, the device is characterized in that the generator is a radio frequency generator for the delivery of radio frequency energy for nerve ablation.

In one embodiment, the device is characterized in that the conformable support further comprises at least one sensor adapted to sense a physical parameter, or physiological parameter of the subject. In one embodiment, the at least one sensor is adapted to reveal the position of a nervous tissue in the periphery of a blood vessel and feedback-activate a generator operably connected to the plurality of the electrodes so that one or more electrodes deliver spatially-selective electrical energy to the nervous tissue.

In one embodiment, the device is characterized in that it further comprises means for fixedly grafting to the internal wall of a blood vessel.

In one embodiment, the device is characterized in that a distal portion thereof comprising the conformable support is detachable from the rest of the device.

In a particular embodiment, the device is characterized in that the actuator is included within the distal, detachable portion.

Another aspect of the invention relates to a method for treating or preventing a pathological condition in a subject in which an electrical nerve modulation could be beneficial by using the above-described device, characterized in that it comprises the following steps:
  a) reaching a target blood vessel of the subject in proximity with a nervous tissue by advancing the tubular element through an access point;
  b) adapting the radius and/or the pitch of the helically configured portion of the conformable support via an actuator's driven extension, retraction and/or rotation of the flexible shaft so that the electrodes contact a portion of the endoluminal surface of the target blood vessel;
  c) activating a generator operably connected to the plurality of the electrodes so that one or more electrodes deliver electrical energy to the target blood vessel; and
  d) optionally repeating steps b) and c) for other portions of the endoluminal surface of the target blood vessel.

In one embodiment, the nervous tissue is a nerve forming part of the sympathetic nervous system.

In one embodiment, the nervous tissue is at least one of the group consisting of: the stellate ganglion, the inferior cervical ganglion, the middle cervical ganglion, the superior cervical ganglion, the carotid body, the cavernous plexus, the ciliary ganglion and the pterygopalatine ganglion.

In one embodiment, the target blood vessel is at least one segment of the internal carotid artery in a group consisting of: the cervical section (C1), the petrous section (C2), the lacerum section (C3), the cavernous section (C4), the clinoid section (C5), the ophthalmic section (C6) and the communicating section (C7).

In one embodiment, the electrical nerve modulation is nerve ablation and the generator is a radio-frequency generator.

In one embodiment, the pathological condition is cerebral vasospasm, treatment-refractive hypertension or Raynaud's disease.

BRIEF DESCRIPTION OF DRAWINGS

FIG. 10C shows a possible release process in three steps.

DESCRIPTION OF EMBODIMENTS

Figure 1A:
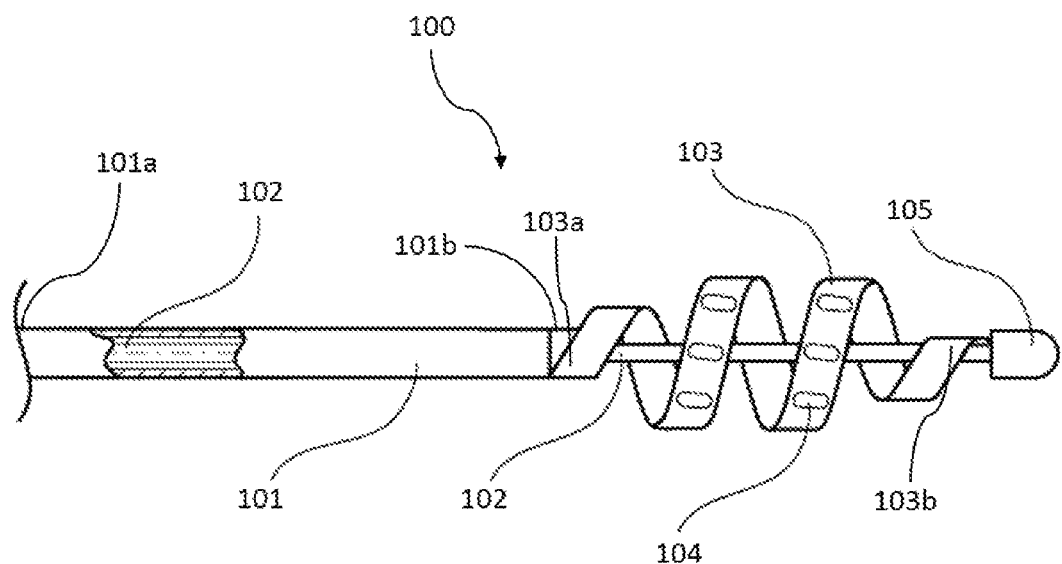
FIGS. 1A and 1B depict a lateral view of one embodiment of the device of the present invention.
Figure 1B:
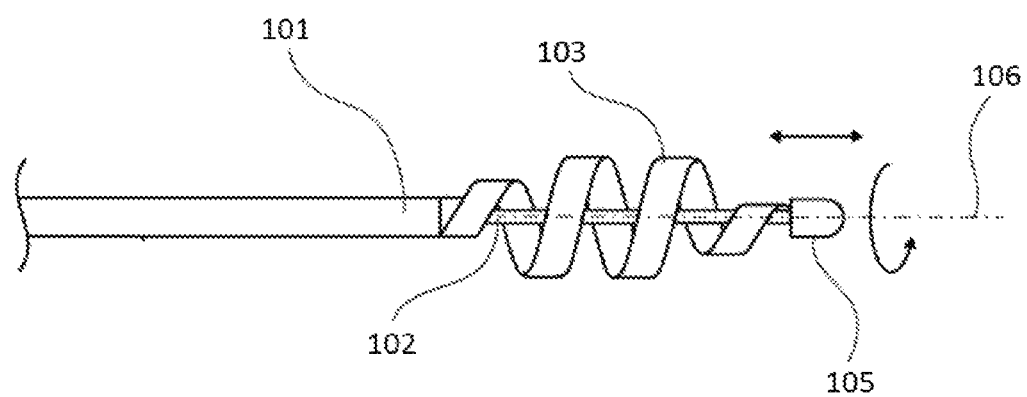
Figure 1C:
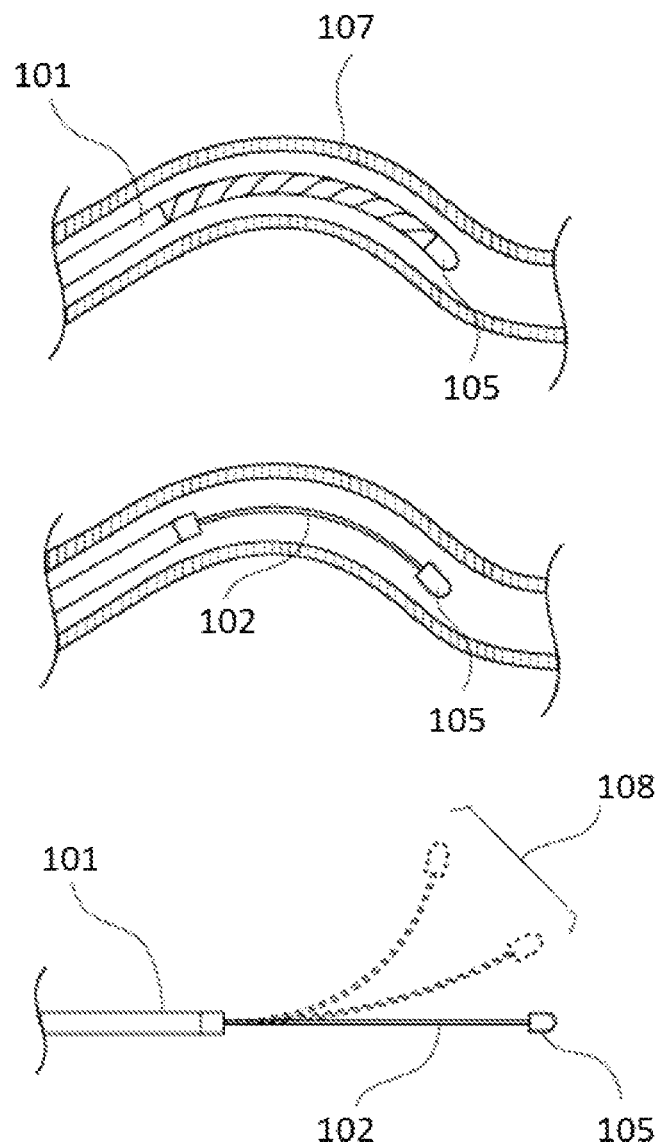
FIGS. 1C and 1D depict respectively a lateral and a frontal view of the device of the present invention inside a blood vessel.
Figure 1D:
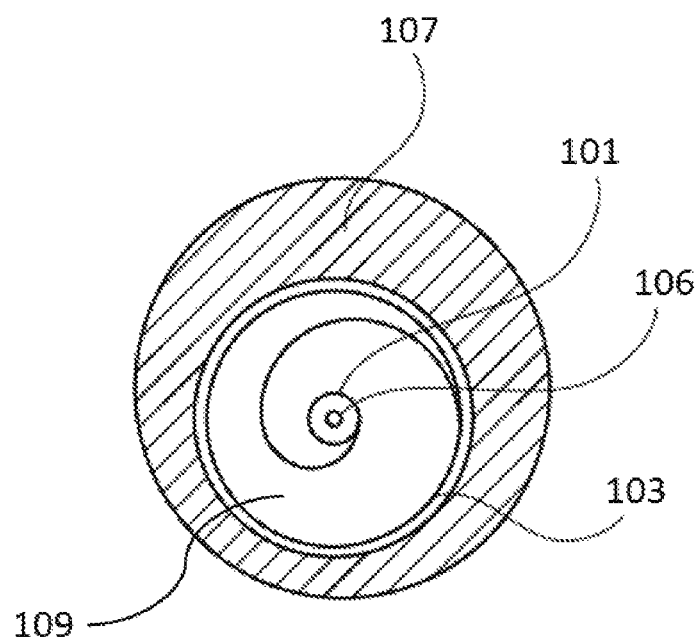
Figure 1E:
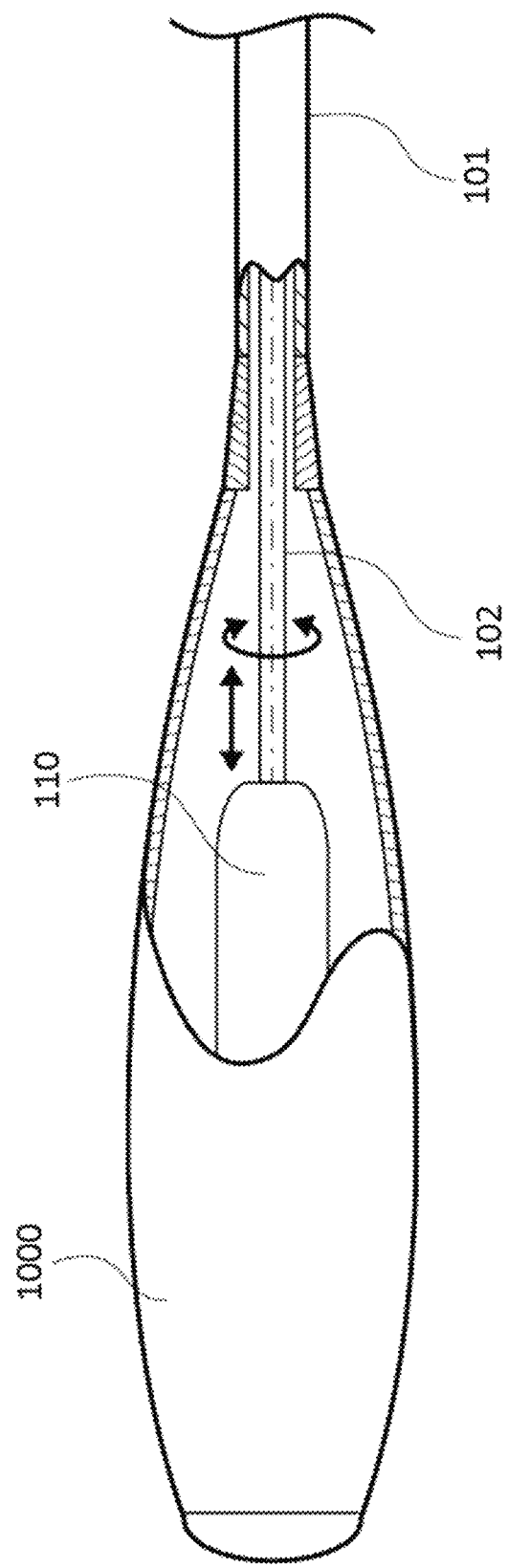
FIG. 1E depicts one embodiment of the device implementing an actuator embedded within a handle.

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Thus, for example, reference to "an electrode" includes a plurality of such electrodes and reference to "a sensor" includes reference to one or more sensors, and so forth.

Also, the use of "or" means "and/or" unless otherwise stated. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of".

With reference to FIG. 1, device 100 according to one embodiment of the invention comprises a hollow tubular element 101 comprising a proximal end 101a and a distal end 101b. The tubular element 101 is basically a conformable catheter-like structure such as those known in the art, preferably made of polymeric, biocompatible plastic materials such as polyurethane, polytetrafluoroethylene (PTFE), fluorinated ethylene propylene (FEP), perfluoroalkoxy (PFA), ethylenetetrafluoroethylene (ETFE), polyether ether ketone (PEEK), polyethylene, polyethylene terephthalate (PET), polyvinylidene fluoride (PVDF), nylon, latex, polyimide, silicone rubber and the like, adapted to be inserted into a natural of artificially created entry opening, and to be slid into a blood vessel of a subject in need thereof. The term "subject" as used herein refers to mammals. For example, mammals contemplated by the present invention include humans, primates, domesticated animals such as cattle, sheep, pigs, horses, laboratory rodents and the like. The tubular element 101 is operably connected to, and extends from, a rotational and linear actuator 110 (FIG. 1E) via its proximal end 101a. As used herein, the wording "operably connected", "operably connectable" or even "operably connecting" reflects a functional relationship between two or more components of a device or a system, that is, such a wording means the claimed components must be connected in a way to perform a designated function. The "designated function" can change depending on the different components involved in the connection; for instance, the designated function of a tubular element 101 operably connected to an actuator 110 is to create a suitable contact between the two elements so that the actuator 110 can suitably operate a flexible shaft, as will be described later on. A person skilled in the art would easily understand and figure out what are the designated functions of each and every component of the device or the system of the invention, as well as their correlations, on the basis of the present disclosure.

A flexible elongated shaft 102 extends all along the tubular element 101, in a substantially coaxial fashion. The flexible shaft 102 comprises a proximal end operably connected to the actuator 110 and a distal end, or tip, 105, and is adapted to be slid along the tubular element 101 upon activation of the actuator 110. The term "flexible", when referred to the shaft 102, designates its capacity to actively or passively bend in one or more direction according to the actuator-driven operation and/or the internal geometry of a blood vessel, as better depicted in FIG. 1C, where device 100 of the invention is shown in operation inside the lumen 109 of a blood vessel 107 in a bent state 108. According to one embodiment of the present invention, shaft 102 can be hollow along at least a portion of its length. This design provides the advantage, in operation during surgical practices, to let a guide wire, commonly used by surgeons, to slide into the shaft 102 in a coaxial fashion and direct the device towards the target site.

Shaft 102 is substantially composed of a conformable, biocompatible material with a semi-rigid nature, or any suitably combination of materials, such as for instance stainless steel, titanium or nitinol. As will be evident to a person skilled in the art, in order to be slid inside the tubular element 101, the shaft 102 has a calibre or a cross-section (depending on the geometries) which is lower compared to that of the tubular element 101, and can generally be comprised between about 10 μm and about 5 mm. Regarding the tubular element 101, its length can range from between about 0.1 and about 5 meters, depending on several factors such as for instance the subject's entry point or the target blood vessel.

Figure 4A:
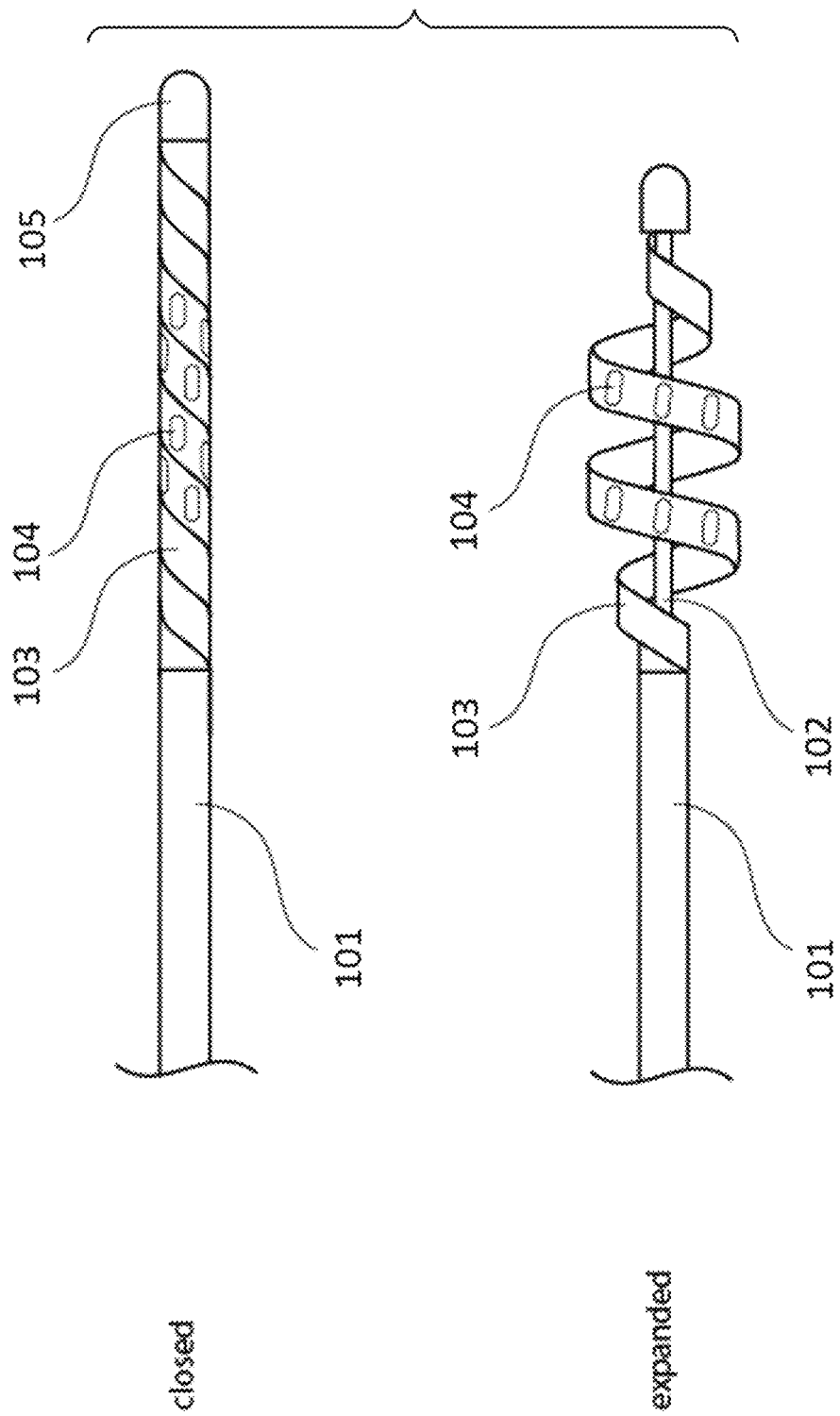
FIG. 4A shows a closed (top) and expanded/deployed (bottom) configuration of the soft support of the device upon linear actuation, with change in radius of the helical geometry of said support (FIG. 4B)
Figure 4B:
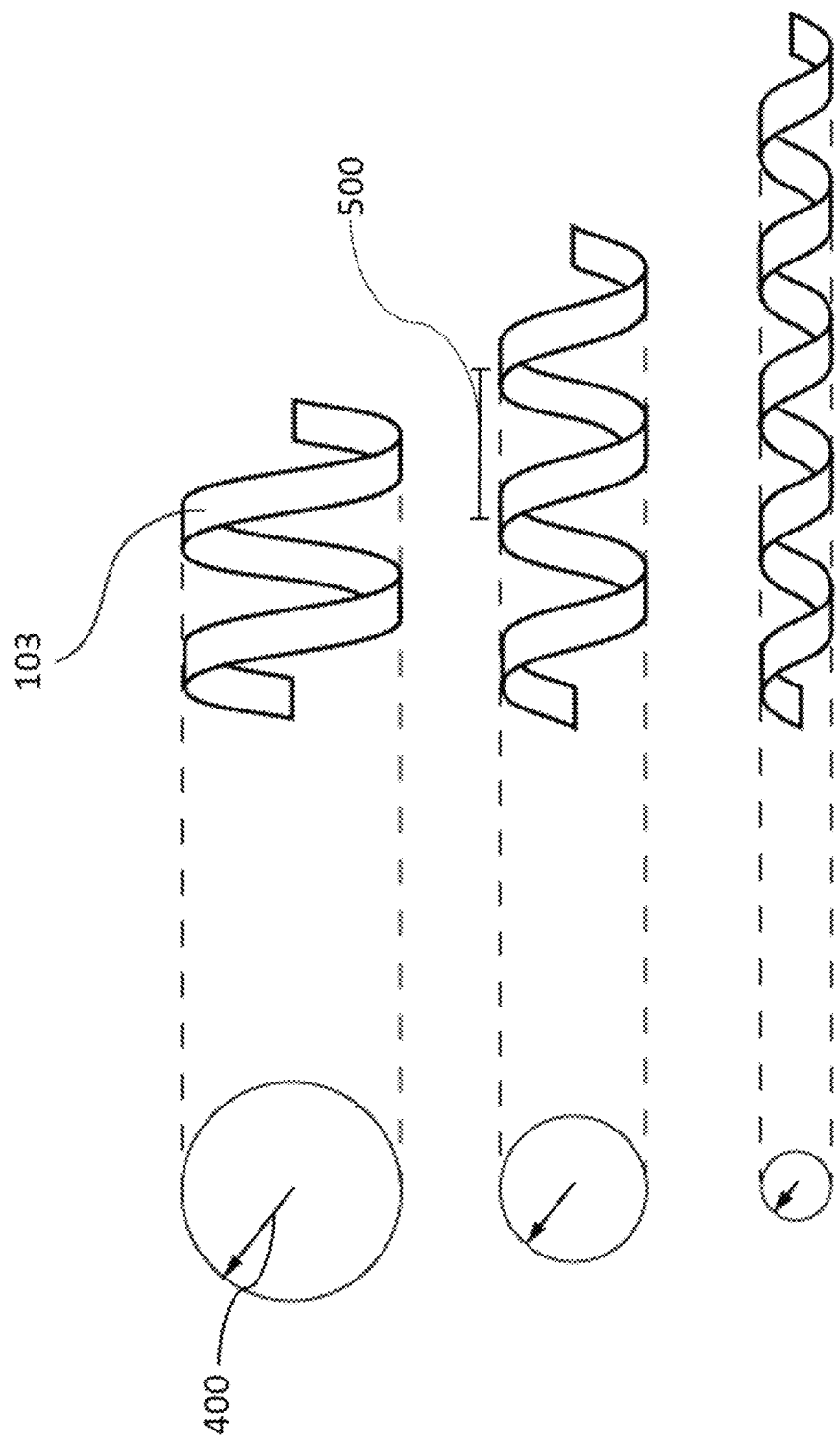
FIG. 4 depicts the linear and rotational actuation of the device of the invention.
FIG. 4C shows the change in the pitch of the helical support upon the rotational actuation of the device, without change in the radius of the helix.
Figure 4C:
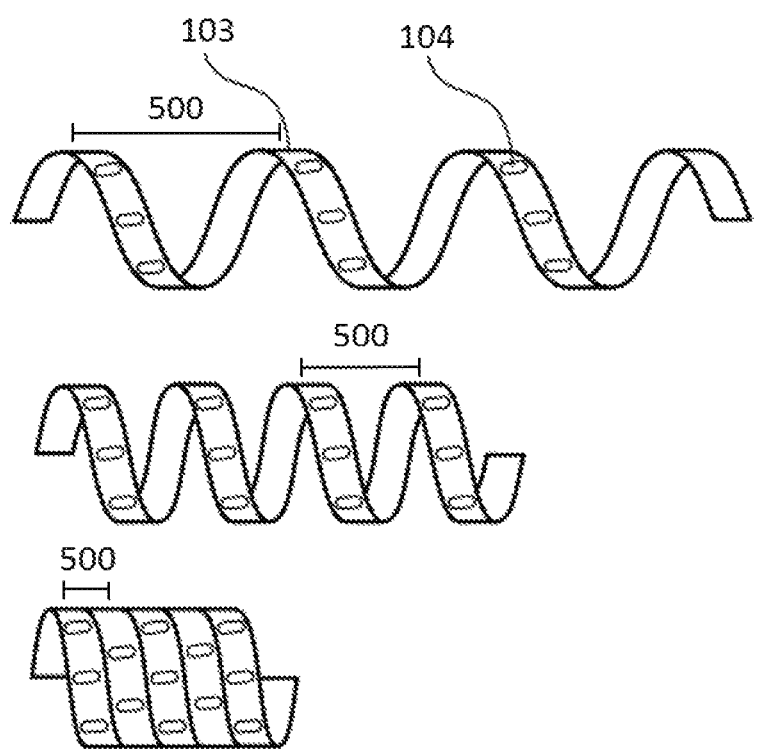

A conformable support 103 is affixed at its distal extremity 103b to the distal end 105 of the shaft 102. The proximal end of support 103 is, on the other hand, connected to the distal end 101b of the tubular element 101. Said conformable support 103 is configured to have at least a distal portion of its length wrapped in a helical fashion about a distal portion of the shaft 102. As will be immediately apparent, a helical configuration of the support 103 defines a cross-sectional radius 400 and a pitch 500 for this element of the device, as depicted in FIGS. 4B and 4C. The "cross-sectional radius" is the radius of a round section of the support 103 having the main axis 106 of the shaft 102 at its centre and the most external portion of the support 103 as circumference in a straight configuration of the device 100. In the same way, the "pitch" is the width of one complete helix turn, measured parallel to the axis 106 of the helix (see for instance FIG. 1B). In preferred embodiments of the invention, the conformable support 103, at least in its central portion, is substantially a circular helix, i.e. it has a constant radius and therefore a constant band curvature and torsion. All the conformable support 103 parameters, particularly its radius 400 and its pitch 500, can be suitably changed and adapted to fit with the blood vessel profile once the device 100 is in operation, as will be described later on, thanks to the activation of the actuator 110 (see for instance FIGS. 1D, 4A and 5).

The conformable support 103 is dimensioned in length according to the length of the shaft 102, which depends in turn on several criteria such as the subject's entry point, the target blood vessel or the type of therapy to be provided to the subject. Support 103 is sized and shaped in the other dimensions (thickness and width) depending on several other factors, such as for instance the need for a good compliance with the internal wall of a blood vessel 107, the material it is composed of, the number or position of electrodes 104 patterned on it and so forth. For instance, in preferred embodiments, the conformable support 103 can have a wire or a ribbon-like structure so to better accommodate the set of electrodes 104 disposed therein, as will be detailed thereafter. Generally speaking, the support 103 can have a variable length of few millimetres up to meters, and a thickness/width in the order of few nanometres up to few millimetres.

Concerning the materials of the support 103, in preferred embodiments this is substantially made of a soft polymeric material, or combinations of many soft polymeric materials, particularly biocompatible ones and possibly dielectrics (118). The term "soft" is herein intended to include any material which is compressible, reversibly compressible, elastic, flexible, stretchable or any combination thereof. Examples of suitable materials for the support 103 are for instance polyurethane, polytetrafluoroethylene (PTFE), fluorinated ethylene propylene (FEP), perfluoroalkoxy (PFA), ethylenetetrafluoroethylene (ETFE), polyether ether ketone (PEEK), polyethylene, polyethylene terephthalate (PET), polyvinylidene fluoride (PVDF), nylon, latex, polyimide, silicone rubber or combinations of any of the foregoing.

To help stabilizing the support 103 in a target position, in one embodiment the device is characterized in that it further comprises means for fixedly grafting to the internal wall of a blood vessel. Grafting means can be integrated at the border of the support 103 and includes shapes like hooks, anchor or any regular or irregular jagged shapes a tissue could grow against/on and grasp in. Other grafting means can take the shape of through holes or any through-shapes at the border of the support or in-between electrodes position.

Figure 9:
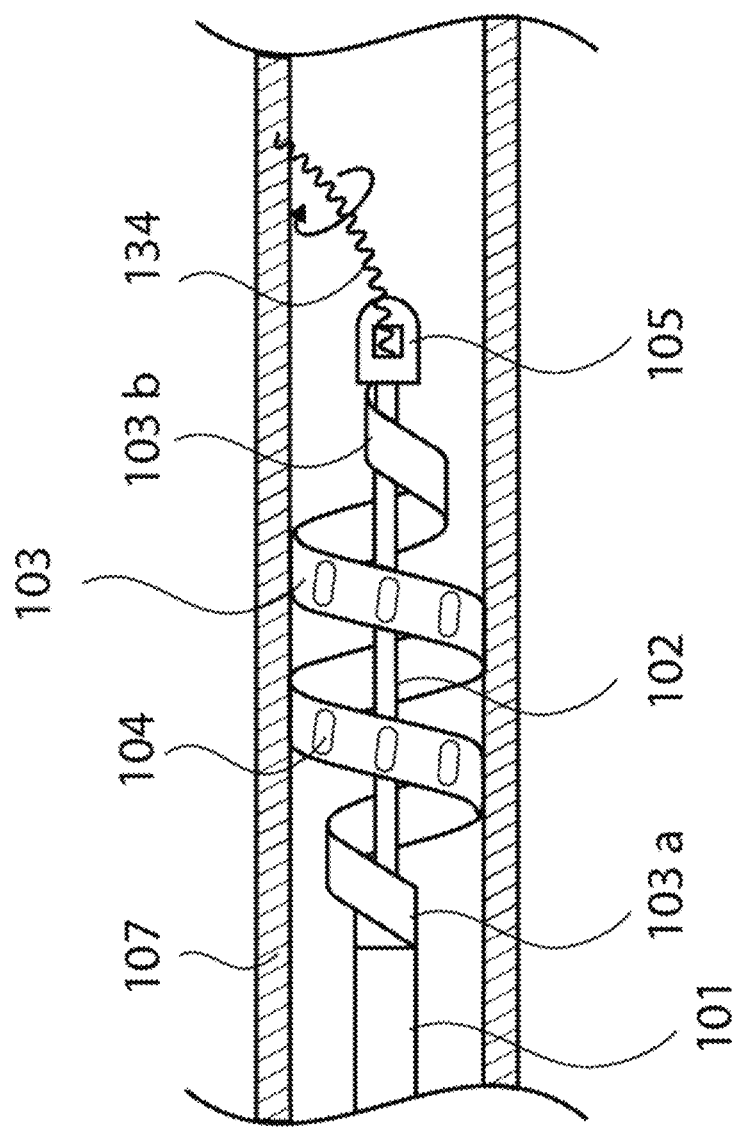
FIG. 9 depicts one embodiment of suitable grafting means for anchoring a distal portion of the device to the endoluminal vessel wall.

Another grafting/fixation mean could relies in biological glue spotted on the support 103, possibly protected until the surgeon decides to deploy the mechanism and later solidify the glue at the contact of the vessel wall 107. In one scenario, grafting means are embodied as an additional micro-system 134 preferably positioned at the distal portion of the device 100, such as for instance at the tubular element's distal end 101b, at the tip 105 of the shaft 102 or even both. The grafting means 134 can interact with the elements of the device 100 and with a blood vessel 107 in many ways; for example, grafting means 134 can be embedded within the distal end 101b and/or the tip 105 as a deploying element activated through the actuator 110, that can grasp and fix into/onto the internal wall of a blood vessel 107 via e.g. a coil-like structure 134a which anchors to the vessel wall through rotation (FIG. 9). The grafting means 134 can prove particularly useful in those embodiments of the invention where a distal portion of the device, comprising at least the conformable support 103 and all or some of its physically associated structures, is detached from the rest, and persists within a subject in the form of a fixed, active electrical-modulation implant, as will be detailed later on. In fact, in view of the highly dynamic environment of a blood vessel, which is subject to many physical stimuli such as contractions, dilatations or the simple pulsatile blood flow, it is vital for such an implant to guarantee its precise and durable positioning within a target area of the vessel, with no or limited room for errors.

Figure 2A:
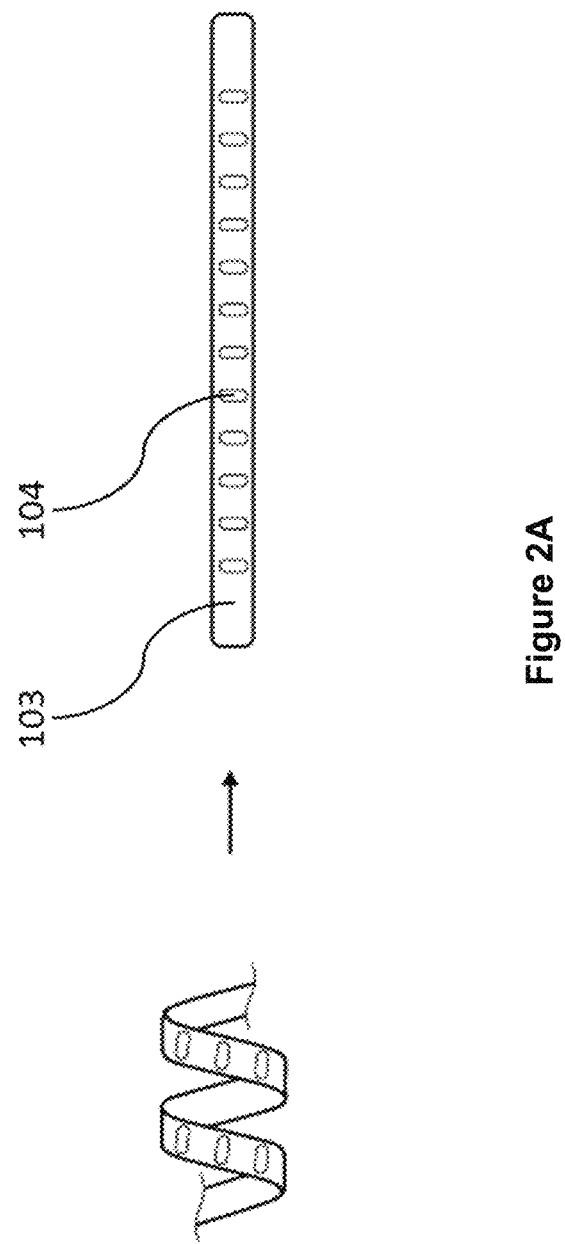
FIG. 2A depicts a top view of a helically wrapped (left) and unwrapped (right) conformable support patterned with electrodes.
Figure 2B:
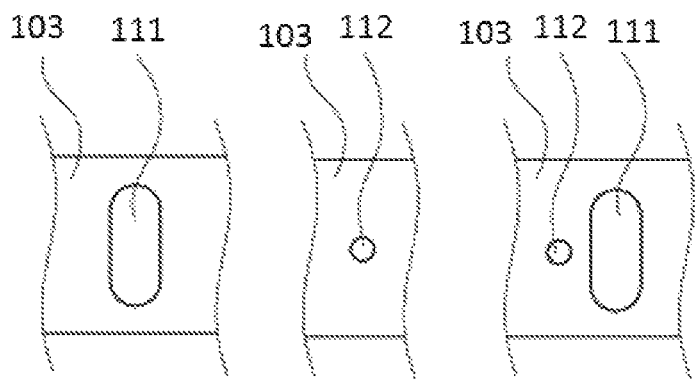
FIGS. 2B to D depict several embodiments of the disposition of the electrodes and sensors in and on the conformable support.
Figure 2B:
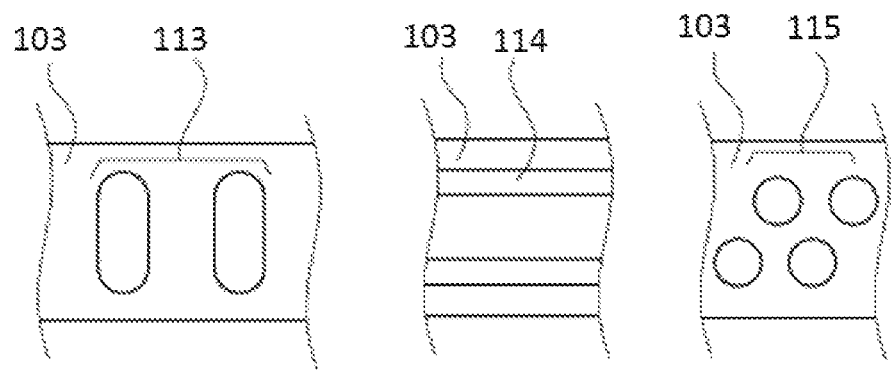
Figure 2B:
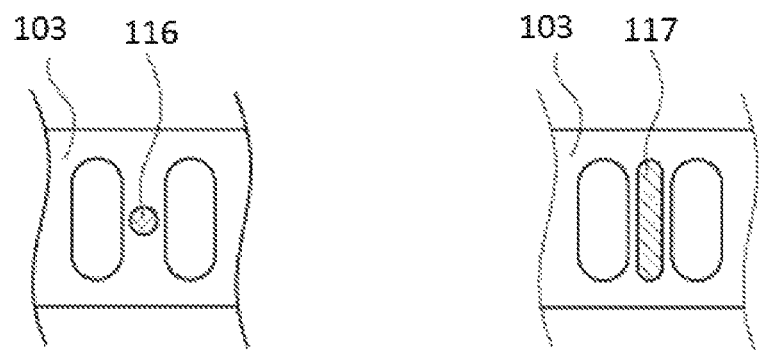

Along the helically configured portion of the conformable support 103 are disposed a plurality of electrodes 104 adapted to contact the endoluminal surface of a blood vessel 107 of the subject, and deliver electrical energy once electrically connected to a generator 200. FIG. 2A depicts a top view of a non-helically wrapped conformable support 103 comprising a set of electrodes 104 according to one embodiment of the invention. Electrodes 104 can be disposed along the helically-coiled portion of the support 103 with any suitable configuration, depending on the needs; for instance, single electrodes 104 can be evenly disposed at regular intervals (e.g. one each helix turn) or at otherwise predetermined intervals, or bundles/groups of electrodes 104 can be present, regularly or irregularly disposed on the support 103. Embodiments envisaging the presence of groups of electrodes 104 are particularly convenient when these must be activated in a bi- or multi-polar fashion. In fact, as will be explained in more details later on, a key feature of the device 100 of the invention is its ability to work in a bi- or multi-polar modality so that a more precise and efficient electrical modulation can be provided to a nervous tissue. For instance, with reference to FIG. 2B, couples of electrodes 113 can be suitably disposed on the support 103, also in the form of band electrodes 114, or otherwise a plurality of electrodes 115 can be patterned and grouped on the support 103 in any convenient arrangement or number. Depending on the applications, the electrodes 104 can be stimulatory electrodes 111 adapted for electrostimulation or recording electrodes 112 for sensing physiological parameters of nervous tissues such as electrical currents, nerve functionality, or both.

Figure 2C:
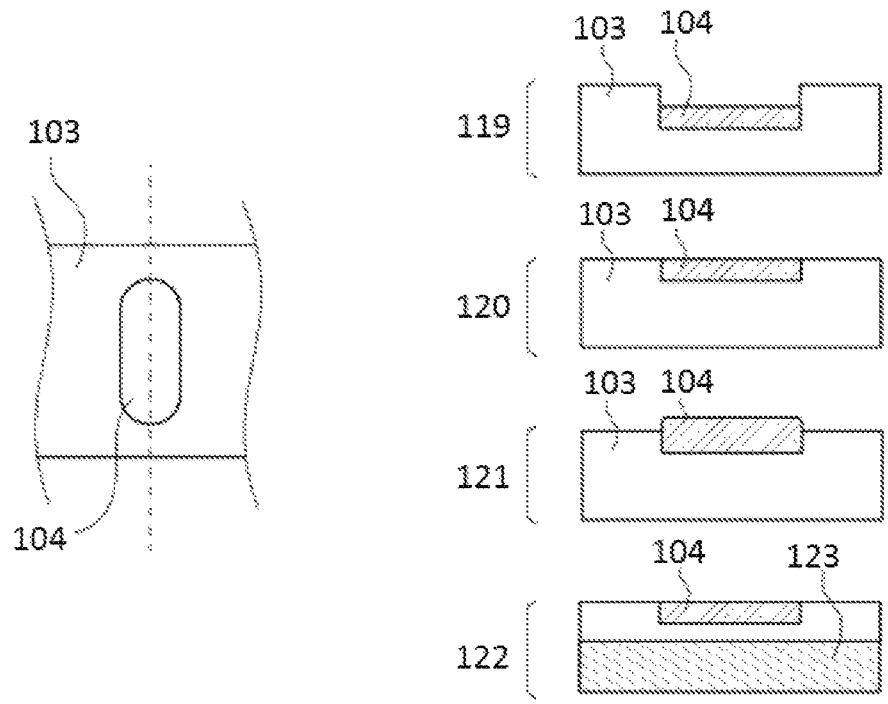
Figure 2D:
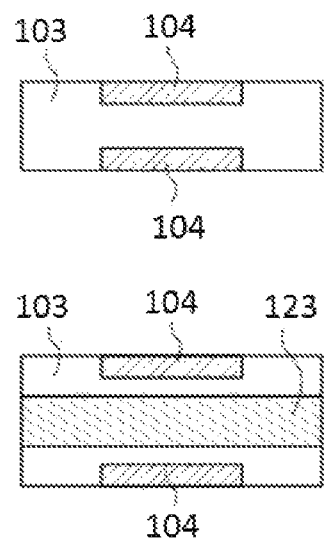

Electrodes 104 can have any suitable shape such as round, square, elliptical or rectangular, and can be made of any suitable electrical conductive material, including but not limited to metals such as Au, Pt, Al, Cu and the like, as well as any alloy thereof, oxide thereof and combinations thereof, composite metal-polymer materials and so forth. In a preferred embodiment, the electrodes are made of non-toxic and biocompatible materials. Electrodes 104 can be placed on the support 103 with any suitable means such as for instance photolithography, electron beam evaporation, thermal evaporation, sputter deposition, chemical vapour deposition (CVD), electro-plating, molecular beam epitaxy (MBE) or any other conventional mean known in the art. Moreover, as depicted in FIG. 2C showing a transverse cross-section view of a support 103 with an electrode 104 patterned on it, electrodes 104 can be arranged in a step down configuration (119), flat configuration (120), step up configuration (121) and/or a mixed assembly configuration (122), in which a flexible, band-like element 123 such as a nitinol film or wire can serve as an additional mechanical support element for the support 103.

In some embodiments of the invention, electrodes 104 are compliant electrodes. A "compliant electrode" is any structure or element able to deliver an electric current, and adapted to change its shape according to the shape change of the support it adheres to, without substantially compromising mechanical and/or electrical performances. The term "compliant" is intended to include any conformable structure which is compressible, reversibly compressible, elastic, flexible, stretchable or any combination thereof. Examples of complaint electrodes known in the art include metal thin-films (including patterned electrodes, out-of-plane buckled electrodes, and corrugated membranes), metal-polymer nano-composites, carbon powder, carbon grease, conductive rubbers or conductive paints, a review of which is provided in Rosset and Shea (Applied Physics A, February 2013, Volume 110, Issue 2, 281-307), incorporated herein in its entirety by reference. In one embodiment, stretchable electrodes as the one described in International Patent Application WO 2004/095536, incorporated herein in its entirety by reference, can be used.

Figure 6A:
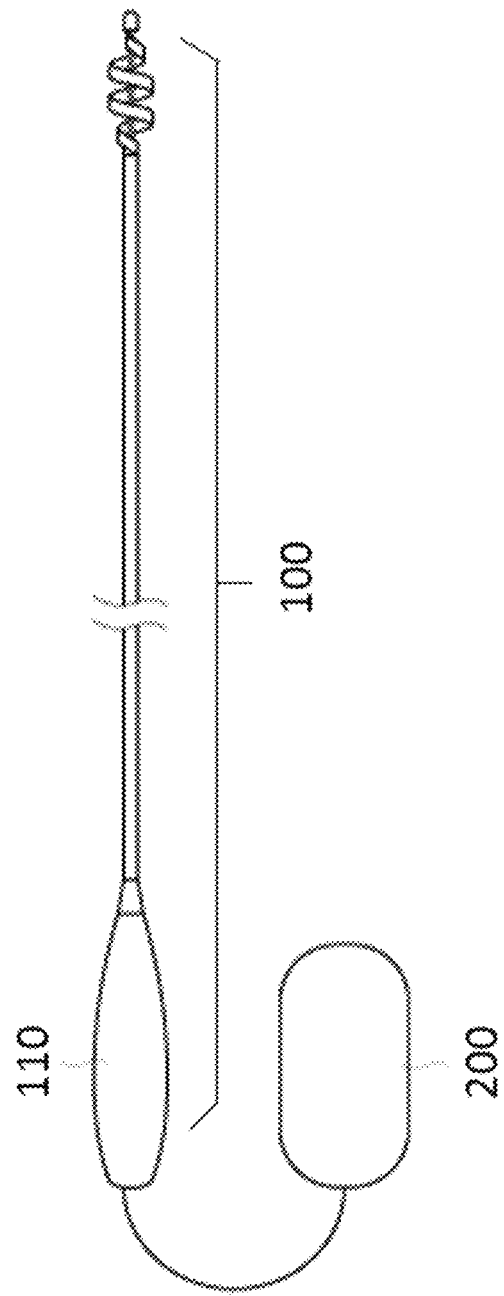
FIG. 6A shows a system comprising the device of the invention operably connected to an electricity generator/modulator such as a radio-frequency generator.

The electrical connection between electrodes 104 and an external generator 200 can be done in any suitable way. With reference for instance to FIGS. 1A and 6, in one embodiment some connection wires (not shown) run from the generator 200 along the tubular element 101 structure up to its distal end 101b, where an electrical pad electrically couples said wires to a circuitry patterned on the support 103 and in turn to electrodes 104.

A further advantage of the device 100 of the invention relies in possibility of activating the electrodes in a mono-, bi- or multipolar fashion, as well as any suitable combination of the foregoing. Monopolar stimulation basically produces a current in which the energy pulse diffuses from a negative pole through a material in the "way of the least resistance". In this case, one or more of the contacts are programmed as negative poles against a ground. This kind of stimulation provides a roughly radial current diffusion that covers an approximately spherical space around the electrode with a relatively high volume of tissue concerned during stimulation, and it may therefore influence a larger target area, particularly when the current density is relatively high. A bipolar stimulation produces a concentrated current around and between the electrodes in which electrons run from the negative to the positive pole, thus creating a narrower and more focused current field. Monopolar stimulation usually has a higher efficacy in terms of energy delivery compared to bi- or multipolar stimulation, but is however normally associated also with a higher rate of side-effects such as for instance exaggerated damage of the surrounding body structures. Activating the electrodes 104 in a bi- or multipolar fashion allows not only a specific, even dynamic, customization of the energy delivered to the nervous tissues, with reduction of side-effects, but also e.g. a complete annular distribution of the energy that can be especially useful in an ablation scenario.

In some embodiments, device 100 comprises one or more suitable sensors for detecting and/or storing at least a subject's physical or physiological parameter. A "sensor" as used herein is a device that detects (and possibly responds to) signals, stimuli or changes in quantitative and/or qualitative features of a given system, or the environment in general, and possibly provides a corresponding output. According to the invention, a sensor preferably comprises a means for detecting and/or storing user's physiological or physical parameters. The sensor can also comprise a data storage device to hold information, process information, or both. The information detected and possibly collected by said sensor can relate to a user's physiological or physical parameter; for instance, a pressure sensor 116 or a temperature sensor 117 (FIG. 2B) is e.g. connected to electrical wires and disposed on the support 103, preferably close to, or at the same location as, the electrodes 104 or groups of electrodes (113-115). As it will be evident, sensors 116-117 are placed on the support 103 so to contact the endoluminal surface of a blood vessel 107 and sense physical or physiological parameters of said blood vessel, but sensors can also additionally or alternatively face the endoluminal cavity, depending on the needs and the physiological or physical parameters to sense.

The sensors further comprise means for transmitting the detected and/or stored data concerning the above-mentioned parameters to external devices such as a computer. Said sensors can work in an open or feedback-loop fashion, i.e. for simply gathering physiological information of the subject or for feedback-influencing the electrodes' 104 activity based on the sensed information, thanks to inputs obtained from e.g. a computer. In some embodiments, those sensors can work in a wireless mode.

Figure 3A:
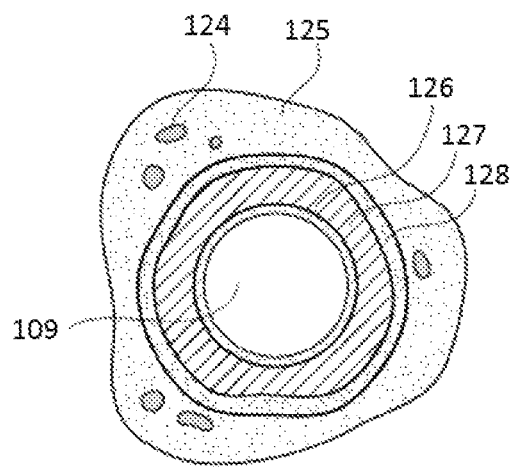
FIG. 3A shows an example of a target artery for nerve modulation.
Figure 3B:
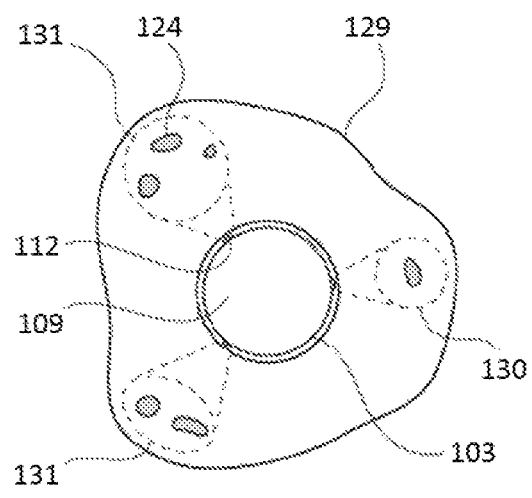
FIGS. 3B and C show the electrode sensing (3B) and modulation via energy delivery (3C) of the nervous tissues disposed in/around a target artery.

In some embodiments, sensing electrode 112 act as sensors, and are adapted to reveal the position of a nervous tissue in the periphery of a blood vessel 107, and feedback-activate a generator 200 operably connected to a plurality of stimulation electrodes 111 so that one or more thereof deliver spatially-selective electrical energy to the nervous tissue. This particular embodiment is depicted in FIG. 3. According to this embodiment of the invention, device 100 is inserted into the lumen 109 of a blood vessel 107, exemplarily depicted in FIG. 3A as a small artery comprising nerves 124, tunica adventitia 125, an endothelium 126, tunica media 127, external elastic tissues 128 and the external limit of connective tissues 129. Once in operation, sensing electrode 112 are suitably activated so to reveal areas comprising single nerves (130) or multiple nerves (131) (FIG. 3B). Since the peripheral nerves constantly transmit signals which are propagated via successive depolarization at the Ranvier Nodes, these local depolarizations, close to the Ranvier nodes, can be detected by exploiting sensing electrodes 112 contacting the endoluminal wall 107. Among all sensing electrodes at the periphery of an artery, the ones that detect the strongest signal, which could be also possibly externally induced, are the ones that are the closer.

Figure 3C:
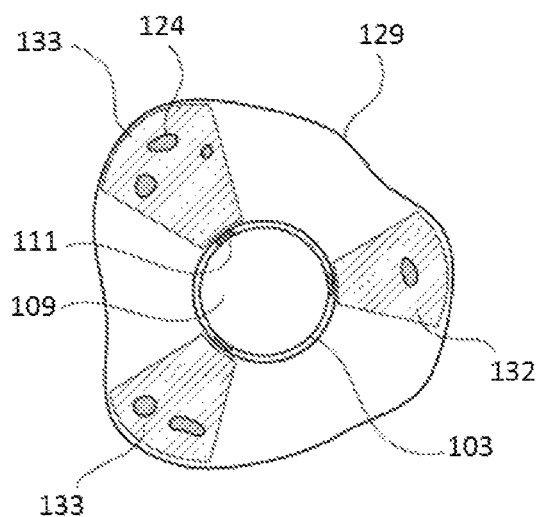

Based on this sensing action, stimulation electrodes 111 can be feedback activated via an external generator 200 to deliver a suitable electrical nerve modulation energy, including radio frequency energy for nerve ablation, to single (132) or multiple (133) modulation regions. The preliminary identification of the position and the number of nervous tissues (e.g. nerves) along a blood vessel 107 through sensing electrodes 112 allows an optimized energy delivery for the modulation of said nervous tissues, thus tailoring the treatment and reducing as far as possible any side effect due to random energy distribution (FIG. 3C).

As said, the actuator 110 is operably connected to the flexible shaft 102 so to slide it along the tubular element 101. However, the flexible shaft 102 can in addition be operated so to rotate about its long axis 106. In this context, when in use, device 100 is inserted into position within a blood vessel 107 to be treated. In one embodiment of the invention, as shown in FIG. 4A, to facilitate insertion into a patient's vessel 107, device 100 is delivered in the "closed" configuration, in which the shaft 102 is disposed in its maximally extended position and the support 103 is disposed in its maximally stretched disposition and thus wrapped relatively tightly about shaft 102, collapsing the helix and thereby reducing the radius 400 at maximum and at the same time also the pitch 500. Once put the device 100 in the target position within the vessel 107, an operator can then operate the actuator 110 so to withdraw the shaft 102 and pull its distal end 105 toward the actuator 110, thus collapsing the helix of the support 103 and increasing the radius 400 of the coiled support 103 while reducing its pitch 500, so to change the longitudinal and radial location of the several electrodes 104 (FIGS. 4A and 4B). However, a key feature of the device 100 of the present invention relies in the possibility to change the position of electrodes 104 while keeping constant and fixed a precise radius 400. This is accomplished thanks to the possibility to rotate the shaft 102 through the actuator 110: a rotation in the sense of the curvature of the helical support 103 will pack said support by reducing the pitch 500, while a rotation in the sense opposed to the curvature of the helical support 103 will deploy this latter by augmenting the pitch 500 (FIG. 4C).

The possibility of fine-tuning the pitch 500 through an actuator-driven rotation of the shaft 102 opens several opportunities in terms of precise and personalized treatment of a pathological condition benefiting from a nerve electrical modulation. In fact, contrary to what is known in the art, once a support comprising a plurality of electrodes is placed or deployed so to be in closed proximity to the internal wall of a blood vessel, the relative position of the electrodes remains fixed or can be altered with a limited degree of freedom, which is function of the structural geometry of the support including them. For instance, a device as the one described in US 2015/0126992 allows the placement of electrodes with a limited range of positions, dictated by the length of the support, the curvature thereof, the length of the shaft and the like, thus impairing for instance an ad hoc, even dynamic, positioning of the said electrodes in areas of interest or with an increased density in particular locations. On the other hand, providing an additional degree of freedom (rotation) to the shaft 102 in the device of the invention allows a proper, customized disposition of the energy-delivering elements, and therefore eventually a more efficient treatment of the vessel target regions.

The actuator 110 can be operated in any suitable way, such as through manual means, pneumatic means, hydraulic means, electromechanical means or computer-assisted means, as well as suitable combinations thereof as in case of a robotic system operably connected to the actuator 110 or forming part of this latter. For instance, the actuator 110 can include a guided slider mechanism or other means for enabling extension, retraction and rotation of the shaft 102 such as a pivotable lever and fork, a user engageable pivotable lever-driven gear and rack attached to the proximal portion of the shaft 102, a thumb wheel driven screw attached to the shaft 102, a thumb driven rotatable pinion and rack attached to shaft 102, a simple hydraulic or pneumatic actuator of any type; a ball or lead screw actuator, or a low voltage electrical motor driven version of any of these. For enhancing the manoeuvrability of the entire device, the actuator 110 can be included into a handle 1000 (FIG. 1E) which can be easily used by a physician or otherwise an operator; in one scenario, the handle 1000 can comprise activating/regulating knobs, buttons, levers or combinations thereof for an ameliorated and facilitated activation experience. All the electrical components of the device 100, including the actuator 110 and the electrodes 104, can be activated via embedded (rechargeable) batteries, wired connections to one or more external power supply, as well as in a wireless mode, for instance through (resonant) inductive coupling, (resonant) capacitive coupling, magnetodynamic coupling, ultrasounds and/or infrared radiation, by the simple implementation of solenoid antennas in any suitable position within the device. As will be evident for a person skilled in the art, the actuator 110 can in some embodiments also be operated in any suitable wireless way, and also in a virtual reality context, and it can also be imagined in a miniaturized, embedded version.

Figure 6B:
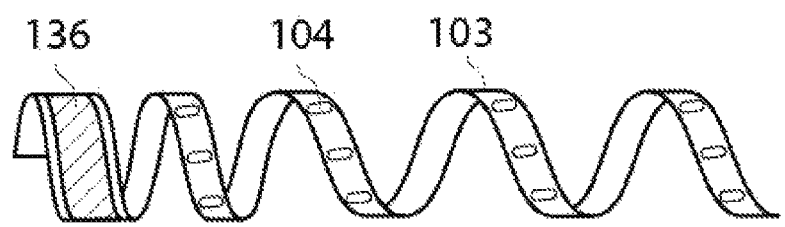
FIG. 6B shows one embodiment of a permanent implant including the conformable support and the associated electrodes.
Figure 6C:
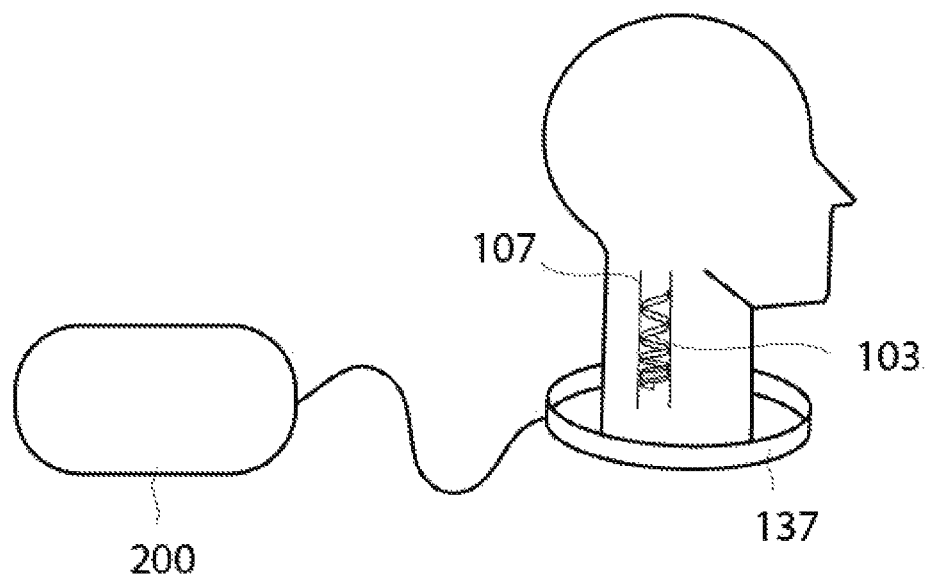
FIG. 6C shows the same implant in operation within a human subject, wirelessly connected to and powered by an external generator/connecting unit.
Figure 7:
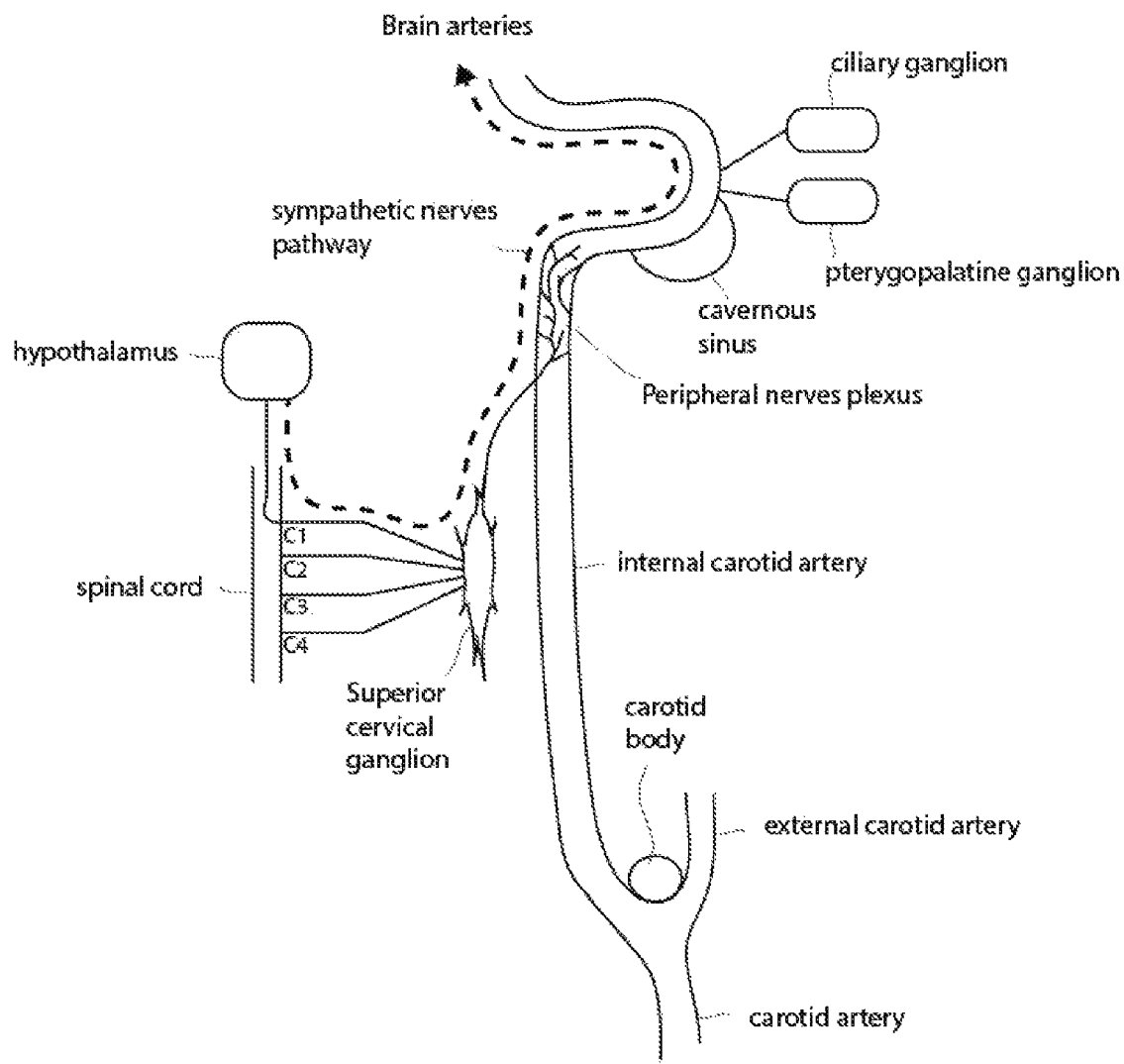
FIG. 7 depicts the internal carotid structure and its connection with the sympathetic nervous system, showing the sympathetic pathway.

An additional aspect of the invention relies in a permanent implant for use in electrical nerve modulation in a subject, characterized in that it comprises at least the conformable support 103 and the associated electrodes 104, as exemplary depicted in FIG. 6B. This particular aspect is linked to the necessity in some context to provide a long term, dynamic and/or on-demand electrical modulation of certain nervous structures for the treatment or the prevention of chronic, relapsing or durable pathological conditions including neurological conditions such as Alzheimer's disease, Parkinson's disease, Amyotrophic Lateral Sclerosis, epilepsy, Multiple Sclerosis, strokes, brain aneurysms or migraines. Accordingly, a fixed implant, stemming from the device of the invention and exploiting its functional features, is an ideal solution.

Figure 10A:
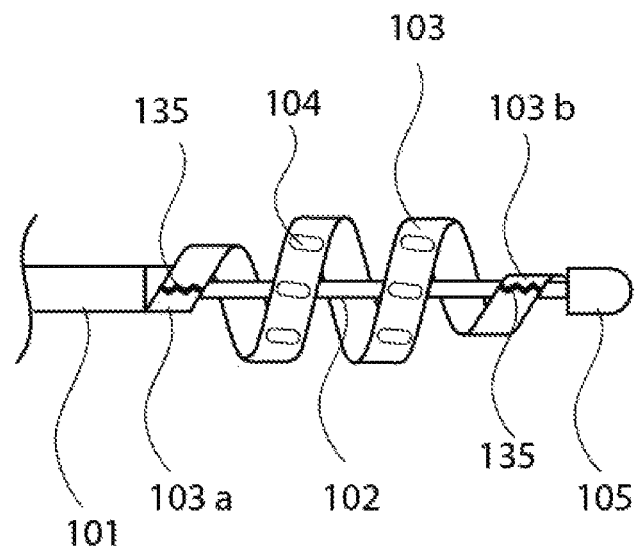
FIG. 10A depicts one embodiment of the position of the detachment points on the conformable support.

In this context, in one embodiment the device 100 of the invention is characterized in that a distal portion thereof, comprising the conformable support 103, is detachable from the rest of the device. Many scenarios are contemplated in this sense. For instance, the above-mentioned distal portion can include the single conformable support 103 and the electrodes 104. In this configuration, the detachable zones 135 are located in the distal and the proximal portions 103 and 103b of the conformable support 103, as shown in FIG. 10A. A signalling element 136 implementing e.g. embedded coil antennas and/or solenoids can be included in a distal or preferably a proximal portion of the support 103 for wireless activation/power supply via e.g. external antenna(s) 137 of the electrodes 104 and possibly the sensors, and can also include additional elements such as microprocessors and data storage means, as shown in FIGS. 6B and C.

Figure 10B:
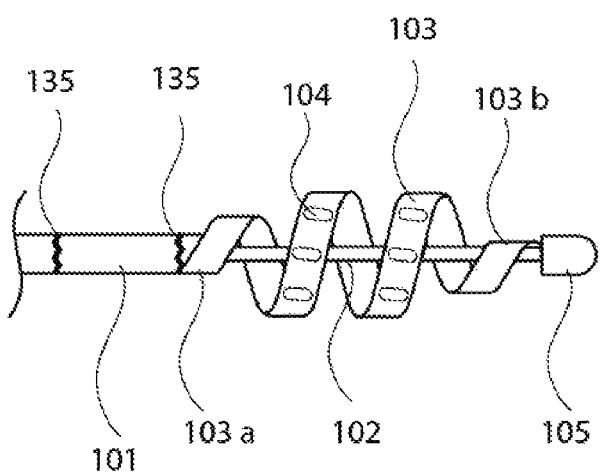
FIG. 10B depicts some embodiments of an implant according to the invention comprising the conformable support as well as other structures of the device.
Figure 10B:
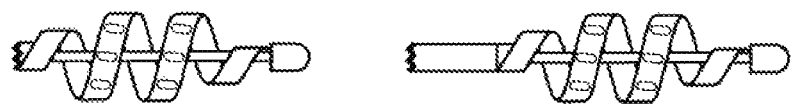

In another configuration, the detachable elements include a distal portion of the shaft 102, the tip 105 and the distal end of the tubular element 101b, as well as of course the conformable support 103 and the associated electrodes 104. The detachment point can be placed close or otherwise near to the distal end 101b, as depicted in FIG. 10B, and can be activated to induce the detachment of the device's active distal portion via the actuator 110. In order to produce a dynamic and/or on-demand electrical modulation, in a particular embodiment the device 100 is characterized in that the actuator 110 is included within its distal, detachable portion, thus forming part of the final implant (FIG. 10). The inclusion in the device of an embedded, miniaturized version of the actuator 110 allows the active operation, especially in wireless mode, of the resulting implant in terms of regulation of the pitch 500 and/or the radius 400 of the support 103.

In one scenario, the conformable support 103 can be detached from the shaft 102 and the tip 105, which are subsequently pulled out with the tubular element 101 once the conformable support 103 has been correctly located within a target blood vessel 107, as shown in FIG. 10C. In another arrangement, the same delivery process can be performed while the elements remaining in the blood vessel further include the tip 105, a distal portion of the shaft 102, a distal portion of the tubular element 101 as well as possibly the actuator 110 as previously described. Once detached from the rest of the device, the electrical components such as electrodes 104 and possibly sensors can be activated wirelessly (via e.g. coil antennas and/or solenoids embedded in the implant) or through embedded batteries, and the "pattern" of electrical stimulation can be provided thanks to a programmable or pre-programmed algorithm implemented in embedded microchip(s) or in external computer device(s) (see for instance FIG. 6C). In this latter case, data storage, data analysis and/or bidirectional communication can be hugely facilitated, either in a static or dynamic way. In the context of the implant of the invention, the inclusion of grafting means 134 is particularly preferred, and these can be implemented at a distal, detached portion of the tubular element 101 (e.g., at the tubular element distal end 101*b*), in the tip 105, on the conformable support 103 or suitable combinations of the foregoing.

An aspect of the invention relates to a method for treating or preventing a pathological condition in a subject in which an electrical nerve modulation could be beneficial by using the device 100 of the present invention, the method being characterized in that it comprises the steps of:

a) reaching a target blood vessel 107 of the subject in proximity with a nervous tissue 124 by advancing the tubular element 101 through an access point;

b) adapting the radius 400 and/or the pitch 500 of the helically configured portion of the conformable support 103 via an actuator's 110 driven extension, retraction and/or rotation of the flexible shaft 102 so that the electrodes 104 contact a portion of the endoluminal surface of the target blood vessel 107;

c) activating a generator 200 operably connected to the plurality of the electrodes 104 so that one or more electrodes 104 deliver electrical energy to the target blood vessel 107; and d) optionally repeating steps b) and c) for other portions of the endoluminal surface of the target blood vessel 107.

As used herein, "treatment", "treating" and the like generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" or "treating" as used herein covers any treatment of a disease in a mammal, particularly a human, and includes: (a) inhibiting the disease, i.e., arresting its development; or (b) relieving the disease, i.e., causing regression of the disease and/or its symptoms or conditions such as improvement or remediation of damage. The term "prevention" or "preventing" relates to hampering, blocking or avoid a disease from occurring in a subject which may be, for any reason, predisposed to the disease but has not yet been diagnosed as having it for example based on familial history, health status or age.

Figure 8:
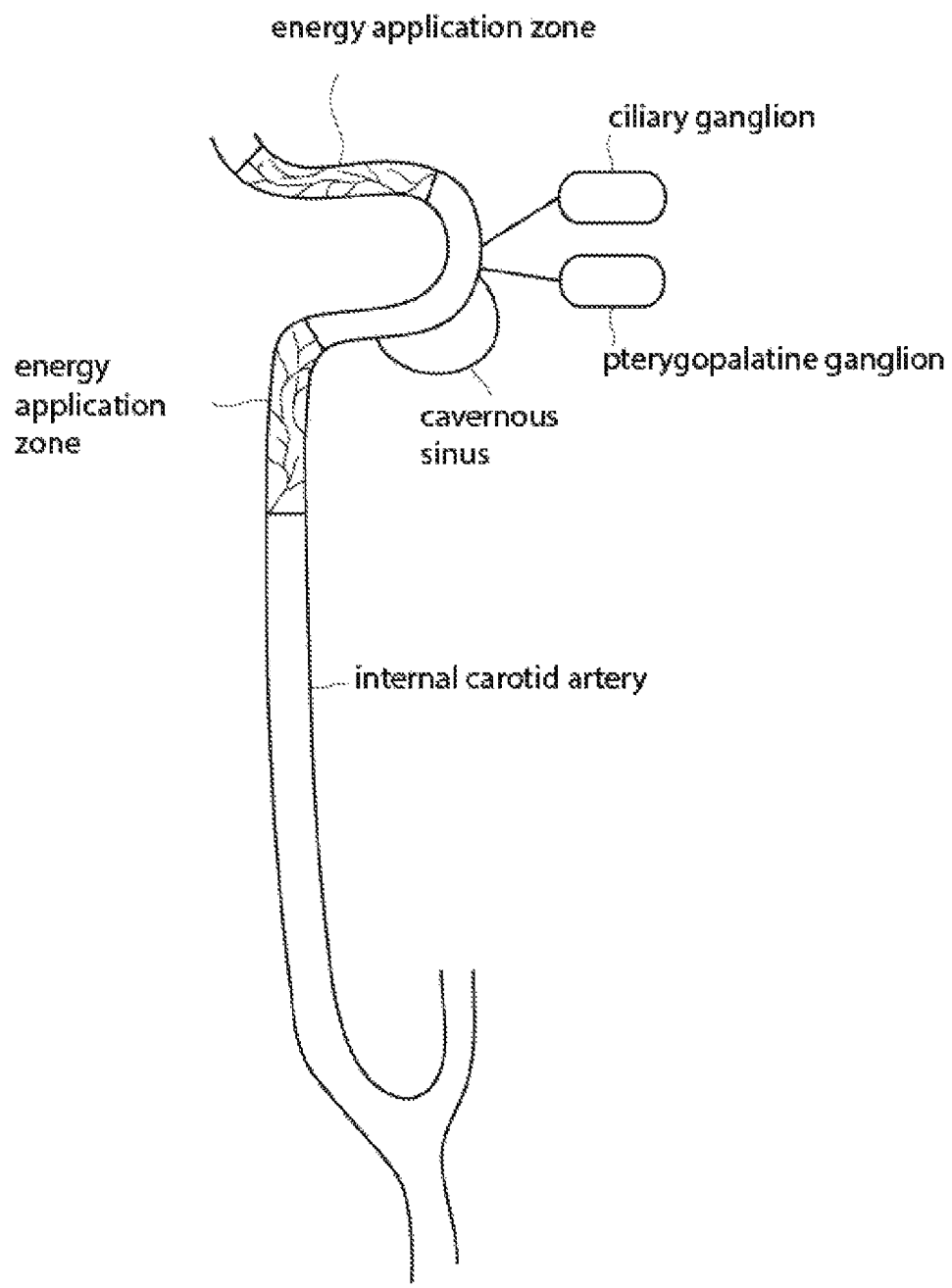
FIG. 8 depicts some segments of the internal carotid artery suitable for energy delivery in case of electrical energy delivery of the nervous tissue forming part of the sympathetic nervous system.

In preferred embodiments according to the invention, the nervous tissue 124 is a nerve forming part of the sympathetic nervous system. Device 100 of the invention is particularly intended and useful in some conditions in which a sympathicotonic effect (a stimulated condition of the sympathetic nervous system in which there is increased tonus of the sympathetic system) appears, such as a vascular spasm (e.g. cerebral vasospasm) or elevated blood pressure conditions as congenital, chronic or idiopathic hypertension. Accordingly, in one embodiment, the nervous tissue 124 to be electrically modulated by the device 100 of the invention is at least one of the group consisting of: the stellate ganglion, the inferior cervical ganglion, the middle cervical ganglion, the superior cervical ganglion, the carotid body, the cavernous plexus, the ciliary ganglion and the pterygopalatine ganglion. Therefore, in some embodiments, the target blood vessel 107 is at least one segment of the internal carotid artery comprised in a group consisting of: the cervical section (C1), the petrous section (C2), the lacerum section (C3), the cavernous section (C4), the clinoid section (C5), the ophthalmic section (C6) and the communicating section (C7). These embodiments are preferred in case the pathological condition to be treated by device 100 is cerebral vasospasm, or even other conditions such as Raynaud's disease or Complex Regional Pain syndrome. In this context, cerebral vasospasm can be treated or even prevented upon activation of stimulation electrodes 111 to deliver electrical stimuli adapted to counteract to the vessel constriction, or by ablating via radio-frequency energy one or more of the above-listed nervous structures associated to the internal carotid artery, as schematically depicted in FIG. 8.

In alternative embodiments, treatment-refractive hypertension, i.e. high blood pressure not controlled by medication, can be treated by device 100 by performing radio-frequency ablation inducing renal denervation, wherein nerves in the wall of the renal arteries are ablated by applying radio-frequency pulses to the renal arteries, causing a reduction of sympathetic afferent and efferent activity to the kidney and blood pressure decrease. Clinically, the tubular element 101, in a closed state, will be inserted into a femoral artery and advanced into a renal artery 107 to be treated or ablated. Then, a radio-frequency (RF) generator 200 is operably connected with device 100 via e.g. a cable assembly/connector. RF-ablation electrode(s) 111 will then be deployed by movement of the actuator 110 on the shaft 102 and made to contact the endoluminal surface of the artery 107 as needed. While possibly monitoring various parameters of the engaged endoluminal surface via sensors 116-117 or sensing electrodes 112, a RF energy will be applied via the electrodes 111 to selected sites on the inner arterial surface (126 in the present case) of the artery 107 in order to ablate the renal sympathetic nerves (124 in the present case) contained therein without affecting the abdominal, pelvic, or lower-extremity nerves.

The device of the invention can even be possibly used for the treatment of other pathological conditions involving an abnormal activation of a portion of the sympathetic nerve trunk, through e.g. ablation of relevant nerves anywhere in either of the two sympathetic trunks. Examples of said pathological conditions are Raynaud's disease, hyperhidrosis, Moyamoya disease, migraines, hyperactive bronchial tubes, long QT syndrome, social phobia or anxiety. Further nervous structures can be treated/ablated such as pudendal nerves, mesenteric ganglia, celiac ganglia, coccygeal ganglia, cervical ganglia, splanchnic nerves, or glossopharyngeal nerves for pain (such as cancer-derived or chronic pain) management, treatment of premature ejaculation and other conditions. In some alternative embodiment, Vagus Nerve stimulation (VNS) can be used for the treatment of intractable epilepsy or treatment-resistant depression, while Vagus Nerve blocking can be used to treat obesity. Furthermore, the device can be used in association with other devices and systems to overcome the secondary effects of certain invasive therapies, such as in case of a catheter-induced coronary artery spasm upon coronary catheterization.

Figure 5A:
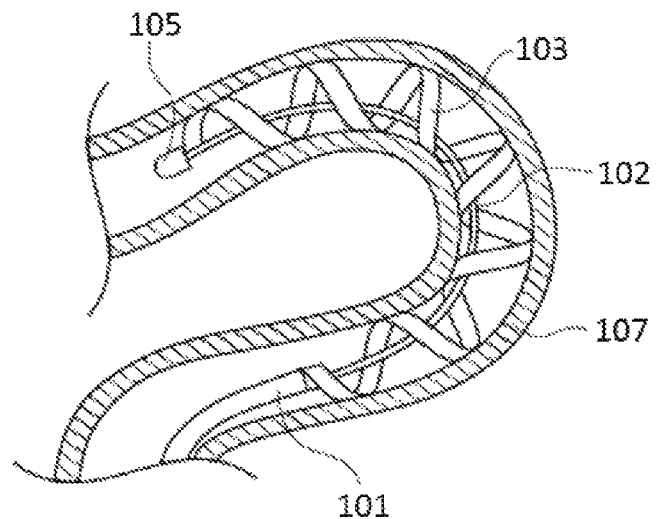
FIG. 5 depict the compliance of the shaft and the support of the device in operation inside a blood vessel, in case of extreme (5A) or slight (5B) vessel curves, or in case of a change of the internal geometry of the vessel lumen due to e.g. a stenosis (5C)
Figure 5B:
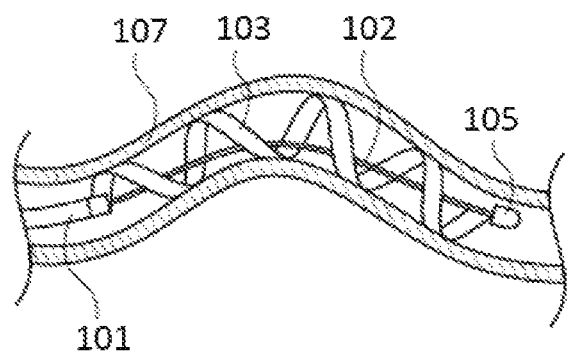
Figure 5C:
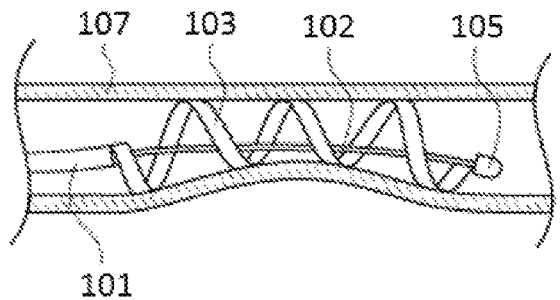

This high versatility of uses of the device of the invention is especially given by its universal design which is adaptable to many, if not all, the sizes and geometries of a blood vessel, which can even change along its length. For instance, as depicted in FIG. 5, the device 100 and particularly shaft 102 and the associated support 103 can conveniently adapt in case of extreme curves (FIG. 5A-B) of a blood vessel 107 as in the case of an internal carotid artery, or lumen 109 cross-section variability (FIG. 5C), which can be fixed in case of a spasm or stenosis of a blood vessel 107, or even dynamically maintain its contact to the lumen of the blood vessel which is permanently moving, due to e.g. the intrinsic movement of blood vessel walls 108 during pulsatile blood flow. Being conformable, support 103 can easily and compliantly adhere to the inner wall of a blood vessel 107 in any situation upon deployment. The additional branching system 134 disposed preferably at the distal end of the device, favours still more the positioning and the fixation of the support 103 on a precise target area within a vessel 107, thus increasing the reliability of the delivered electrical modulation even in a dynamic environment such as an artery.

The invention claimed is:

1. A device for use in electrical nerve modulation in the carotid artery, comprising:
   a) a rotational and linear actuator;
   b) a tubular element having a proximal end connected to the actuator and a distal end;
   c) a flexible shaft coaxially disposed within the tubular element, comprising a proximal end operably connected to the actuator and a distal end, and adapted to be slid along the tubular element;
   d) a conformable support comprising a proximal end operably connected to the tubular element's distal end, and a distal end operably connected to the flexible shaft's distal end, having a portion of its length helically wrapped about a distal portion of the flexible shaft so to define a radius and a pitch;
   wherein the distal portion of the flexible shaft and the conformable support are configured and designed
   (i) to adapt to different sizes and geometries of a blood vessel, and
   (ii) to adapt to curvatures of at least one segment of a carotid artery consisting of a group of a lacerum section, a cavernous section, a clinoid section, an ophthalmic section and the communicating section in a deployed state of the flexible shaft and the conformable support, and
   e) a plurality of electrodes operably disposed along the helically configured portion of the conformable support, and electrically connectable to a generator, adapted to contact the endoluminal surface of a blood vessel of the subject and deliver electrical energy wherein the pitch and radius of the helically configured portion of the conformable support are designed to be modified both independently from each other and jointly via actuator's driven extension, retraction and/or rotation of the flexible shaft,
   wherein the pitch can be modified by rotation of the actuator,
   wherein the electrodes are compliant, and
   the electrodes are only disposed in or on a radially outwardly directed side of the helically configured portion of the conformable support which has a ribbon structure, wherein the ribbon structure is formed, at least in its central portion, by a circular helically configured portion which has a constant radius and therefore a constant band curvature and torsion.

2. The device of claim 1, wherein the conformable support is substantially made of one or more soft polymeric materials.

3. The device of claim 1, wherein the plurality of electrodes are bundled in groups of electrodes.

4. The device of claim 1, wherein the electrodes are activated in a mono-, bi- or multipolar fashion.

5. The device of claim 1, wherein the actuator is operated through manual means, hydraulic means, pneumatic means, electromechanical means, computer-aided means or combinations thereof.

6. The device of claim 1, further comprising a generator operably connected to the plurality of the electrodes.

7. The device of claim 1, comprising a generator, wherein the generator is a radio frequency generator for the delivery of radio frequency energy for nerve ablation.

8. The device of claim 1, wherein the conformable support further comprises at least one sensor adapted to sense a physical or physiological parameter of the subject.

9. The device of claim 8, wherein at least one sensor is adapted to reveal the position of a nervous tissue in the periphery of a blood vessel and feedback-activate a generator operably connected to the plurality of the electrodes so that one or more electrodes deliver spatially-selective electrical energy to the nervous tissue.

10. The device of claim 1, further comprising means for fixedly grafting to the internal wall of a blood vessel.

11. The device of claim 1, wherein a distal portion thereof comprising the conformable support is detachable from the rest of the device.

12. A method for treating or preventing a pathological condition in a subject in which an electrical nerve modulation could be beneficial by using the device of claim 1, comprising the following steps:
   a) Reaching a target blood vessel of the subject in proximity with a nervous tissue by advancing the tubular element through and access point;
   b) Adapting the radius and/or the pitch of the helically configured portion of the conformable support via an actuator's driven extension, retraction and/or rotation of the flexible shaft so that the electrodes contact a portion of the endoluminal surface of the target blood vessel;
   c) Activating a generator operably connected to the plurality of the electrodes so that one or more electrodes deliver electrical energy to the target blood vessel.

13. The method of claim 12, wherein the nervous tissue is a nerve forming part of the sympathetic nervous system.

14. The method of claim 13, wherein the nervous tissue is at least one of the group consisting of: a stellate ganglion, a inferior cervical ganglion, a middle cervical ganglion, a superior cervical ganglion, a carotid body, a cavernous plexus, a ciliary ganglion and a pterygopalatine ganglion.

15. The method of claim 12, wherein the target blood vessel is at least one segment of a internal carotid artery in a group consisting of: a cervical section, a petrous section, a lacerum section, a cavernous section, a clinoid section, a ophthalmic section and a communicating section.

16. The method of claim 12, wherein the electrical nerve modulation is nerve ablation and the generator is a radio-frequency generator.

\* \* \* \* \*